(12) United States Patent
Lam et al.

(10) Patent No.: US 6,444,804 B1
(45) Date of Patent: Sep. 3, 2002

(54) **PROTEINS INVOLVED IN THE SYNTHESIS AND ASSEMBLY OF CORE LIPOPOLYSACCHARIDE OF *PSEUDOMONAS AERUGINOSA***

(76) Inventors: Joseph S. Lam, 2 Bridlewood Drive, Guelph, Onatario (CA), N1G 4A6; Teresa R. De Kievit, 674 Whispering Pines Cir., Rochester, NY (US) 14612; Lori L. Burrows, 1299 Griffith Pl., Oakville, Ontario (CA), L6H 2V8; Andrew Walsh, 223 Terraview Cr., Guelph, Ontario (CA), N1G 5A9; Mauricia Matewish, 139-78 College Ave., Guelph, Ontario (CA), N1G 4S7

(*) Notice: Subject to any disclaimer, the term of this patent is extended or adjusted under 35 U.S.C. 154(b) by 0 days.

(21) Appl. No.: 09/403,768

(22) Filed: Nov. 2, 1999

Related U.S. Application Data

(63) Continuation of application No. PCT/CA98/00395, filed on May 1, 1998, now abandoned.
(60) Provisional application No. 60/045,418, filed on May 2, 1997, and provisional application No. 60/046,149, filed on May 9, 1997.

(51) Int. Cl.$^7$ .................. C07H 21/04; C12N 15/09; C12P 21/04; G01N 33/53
(52) U.S. Cl. ................ 536/23.7; 536/23.1; 435/69.3; 435/71.1; 435/320.1; 435/810; 435/69.7; 435/69.8; 435/71.2; 435/975
(58) Field of Search ................ 536/23.7, 23.1; 435/69.3, 320.1, 71.1, 69.7, 69.8, 71.2, 810; 935/66, 65, 55, 76; 424/260.1, 234.1, 184.1

(56) References Cited

FOREIGN PATENT DOCUMENTS

WO   WO 9014426   * 11/1990

OTHER PUBLICATIONS

Zhao et al. Mammalian Genome 7: 686–690, Sep. 1996.*
Weber et al. Human Molecular Genetics 5 (6): 771–777, Jun. 1996.*
Zhao et al. GenEmbl accession No. U43573, Dec. 1995.*
De Kievit, T.R. et al. "Identification and Characterization of Two Genes, rfaC and rfaF, Involved in *Pseudomonas aeruginosa* Lipopolysaccharide Core Biosynthesis", Abstracts of the Annual Meeting of the American Society for Microbiology, May 19–23, 1996, p. 229. XP002072852. Abstract No. B–429.
Walsh, A.G. et al. "rfa genes of *Pseudomonas aeruginosa*", Abstracts of the Annual Meeting of the American Society for Microbiology, May 4–8, 1997, p. B–211. XP002072856.
De Kievit, T.R. et al. "Isolation and characterization of two genes, waaC (rfaC) and waaF (rfaF) involved in *Pseudomonas aeruginosa* serotype O5 inner–core biosynthesis", Empro Database Entry Pau70982, Accession No. U70982.

De Kievit, T.R. et al. "Isolation and characterization of two genes, waaC (rfaC) and waaF (rfaF) involved in *Pseudomonas aeruginosa* sertoype O5 inner–core biosynthesis", Empro Database Entry Pau70983, Accession No. U70983.
Coleman, Jr., William G. et al. "The rfaD Gene of *Escherichia coli* K–12 and *Pseudomonas aeruginosa* PAO1", Chapter 19, Pseudomonads: Molecular Biology and Biotechnology, 1992. 161–169,
Parker, Craig T. et al. "Identification and Sequences of the Lipopolysaccharide Core Biosynthetic Genes rfaQ, rfaP, and rfaG of *Escherichia coli* K–12", J. Bacteriology, Feb. 1992, vol. 174(3) 930–934.
De Kievit, T.R. et al. "Isolation and Characterization of Two Genes, waaC, (rfaC) and waaF (rfaF), Involved in *Pseudomonas aeruginosa* Serotype O5 Inner–Core Biosynthesis", J.Bacteriology, Jun. 1997, vol. 179(11) 3451–3457.
Klena, John D. et al. "The rfaS Gene, Which is Involved in Production of Rough Form of Lipopolysaccharide core in *Escherichia coli* K–12, is not Present in the rfa Clustero of *Salmonella typhimurium* LT2", J.Bacteriology, Mar. 1993, vol. 175(5), 1524–1527.
Klena, John D. et al., "This rfaS Gene, Which is Involved in Production of a Rough Form of Lipopolysaccharide Core in *Escherichia coli* K–12, is not Present in the rfa Cluster of *Salmonella typhimurium* LT2", GenBank Accession No. S56361.
High, Nicola J. et al. "The role of a repetitive DNA motif (5'–CAAT–3') in the variable expression of the *Haemophilus influenzae* lipopolysaccharide epitope αGal(1–4)βGal", Mol. Microbiology 1993, 9(6), 1275–1282.
High, Nicola J. et al. "The role of a repetitive DNA motif (5'CAAT–3') in the variable expression of the *Haemophilus influenza* lipopolysaccharide epitope αGal(1–4) βGal", GenBank Accession No. L19441.
Sirisena, D.M., et al., "Molecular Analysis of the rfaD Gene, for Heptose Synthesis, and the rfaF Gene, for Heptose Transfer, in Lipopolysaccharide Synthesis in *Salmonella typhimurium*", J. Bacteriology, 1994, 176(8):2379–2385. XP–002072855.
Coyne, M.J. et al., "Sequence Analysis and Characterization of a 4,221–bp segment of the rfa locus of *P. aeruginosa* PAK". PAU63816. Accession No. U63816 (1997), XP–002072859.
Coyne, M.J. et al. Accession No. 033426, (1998), XP002072860.

(List continued on next page.)

Primary Examiner—S. Devi
(74) Attorney, Agent, or Firm—Bereskin & Parr; Micheline Gravelle; Patricia Power

(57) ABSTRACT

Novel nucleic acid molecules encoding proteins involved in the synthesis and assembly of core lipopolysaccharide in *P. aeruginosa;* and novel proteins encoded by the nucleic acid molecules are described. Methods are disclosed for detecting *P.aeruginosa* in a sample by determining the presence of the proteins or a nucleic acid molecule encoding the proteins in the sample.

4 Claims, 12 Drawing Sheets

OTHER PUBLICATIONS

Coyne, M.J. et al. Accession No. 033427, (1998), XP002072861.
De Kievit, T.R., et al. Accession No. 005196, (1997), XP002072862.
Coyne, M.J. et al. Accession No. 033424, (1998), XP002072863.
Coyne, M.J. et al. Accession No. 033425, (1998) XP002072864.
De Kievit, T.R., et al. Accession No. 005195, (1997), XP002072865.

* cited by examiner

Organization of the *waa* Gene Clusters

FIGURE 3

*Pseudomonas aeruginosa waaP*

```
ATGAGGCTGGTGCTGGAAGAGCCGTTCAAGCGCCTGTGGAACGGGCGCGACCCGTTCGAGGCGG
TGGAGGCGCTGCAAGGCAAGGTCTACCGCGAACTGGAAGGGCGCCGCACCCTGCGCACCGAGGT
CGACGGGCGTGGCTACTTCGTCAAGATCCACCGTGGCATCGGCTGGGGCGAGATCGCCAAGAAC
CTGCTCACCGCCAAGCTCCCGGTGCTCGGCGCGCGCCAGGAGTGGCAGGCCATCCGGCGCCTGC
ACGAGGCCGGCGTAGCGACCATGACCGCGGTCGCCTACGGCGAGCGCGGCAGCGATCCGGCGCG
GCAGCATTCCTTCATCGTCACCGAGGAACTGGCGCCGACCGTGGACCTCGAGGTGTTCTCCCAG
GACTGGCGCGAACGTCCTCCACCGCCGCGGCTCAAGCGCGCGCTGGTCGAGGCGGTGGCGCGGA
TGGTCGGCGACATGCACCGTGCCGGAGTCAACCATCGCGACTGCTACATCTGTCATTTCCTGTT
GCACACCGACAAGCCGGTGAGCGCGGACGATTTCCGCCTCTCGGTGATCGATCTGCACCGTGCC
CAGACCCGCGACGCCACGCCGAAACGCTGGCGTAACAAGGATCTGGCGGCATTGTATTTCTCTG
CGCTGGACATCGGACTGACGCGTCGCGACAAGCTACGCTTCCTGCGCACCTATTTCCGCCGGCC
GTTGCGCGAGATACTGCGCGACGAGGCCGGCCTGCTGGCCTGGATGGAACGCCAGGCGGAAAAA
CTCTACGAACGCAAGCAGCGTTACGGAGACCTGCTCTGA
```

FIGURE 4

*Pseudomonas aeruginosa* WaaP

MRLVLEEPFKRLWNGRDPFEAVEALQGKVYRELEGRRTLRTEVDGRGYFVKIHR
GIGWGEIAKNLLTAKLPVLGARQEWQAIRRLHEAGVATMTAVAYGERGSDPARQ
HSFIVTEELAPTVDLEVFSQDWRERPPPPRLKRALVEAVARMVGDMHRAGVNHRD
CYICHFLLHTDKPVSADDFRLSVIDLHRAQTRDATPKRWRNKDLAALYFSALDIGL
TRRDKLRFLRTYFRRPLREILRDEAGLLAWMERQAEKLYERKQRYGDLL

FIGURE 5

```
WaaP_Pa      MRLVLEEPFKRLWNGRDPFEAVEALQGKVYRELEGRRTLRTEVDGRGYFV       50
WaaP_Ec      M-VELKEPLATLWRGKDAFAEVKKLNGEVFRELETRRTLRFELSGKSYFL       49
             * . * **    ** *.* *   * *.* *.**** ***** *. *. **.

WaaP_Pa      KIHRGIGWGEIAKNLLTAKLPVLGARQEWQAIRRLHEAGVATMTAVAYGE      100
WaaP_Ec      KWHKGTTLKEIIKNLLSLRMPVLGADREWHAIHRLSDVGVDTMKGIGFGE       99
             * *.*    ** ****. ..*****  ** ** **  ** **   . .**

WaaP_Pa      RGSDPARQHSFIVTEELAPTVDLEVFSQDWRERPPPPRLKRALVEAVARM      150
WaaP_Ec      KGLNPLTRASFIITEDLTPTISLEDYCADWAVNPPDIRVKRMLIARVATM      149
             .* *     ***.**.*.**. **  .  **    ** *.** *. ** *

WaaP_Pa      VGDMHRAGVNHRDCYICHFLLH---TDKPVSADDFRLSVIDLHRAQTRDA      197
WaaP_Ec      VRKMHTAGINHRDCYICHFLLHLPFTGR---EDELKISVIDLHRAQIRAK      196
             *  ** **.*************    *  .    *. ..********* *

WaaP_Pa      TPKRWRNKDLAALYFSALDIGLTRRDKLRFLRTYFRRPLREILRDEAGLL      247
WaaP_Ec      VPRRWRDKDLIGLYFSSMNIGLTQRDIWRFMKVYFGMPLRKILSLEQNLL      246
             *.*** ***  **** .. **** **  **. . ** *** **  *  **

WaaP_Pa      AWMERQAEKLYERKQRYGDLL    268
WaaP_Ec      NMASVKAERIKERTQRKG--L    265
             **.. **  *    *
```

*Pseudomonas aeruginosa* (Pa) vs *Escherichia coli* (Ec)
Identity = 53.6%

FIGURE 6

```
FEATURES             Location/Qualifiers
     source          1..1038
                     /organism="Pseudomonas aeruginosa"
                     /strain="PAO1"
                     /db_xref="taxon:287"
                     /map="0.3 - 6.6 minutes on the 75 minute linkage map"
     gene            1..1038
                     /gene="rfaF"
     CDS             1..1038
                     /gene="rfaF"
                     /function="adds the second heptose residue onto the core
                     oligosaccharide"
                     /note="RfaF"
                     /codon_start=1
                     /transl_table=11
                     /product="heptosyl transferase II"
                     /db_xref="PID:g1916630"

/translation="MRILIVGPSWVGDMVMAQTLFQCLRQRHPECVIDVLAPEWSRPI

LERMPEVRQALSFPLGHGVMDVATRRRIGRGLRGQYEQAILLPNSLKSALVPWFAGIP

KRTGWRGEMRYGLLNDIRKLDKQRYPLMIERFMALAFEPGVELPKPYPQPRLRIDDGS

RQAALDKFALSLDRPVLALCPGAEFGEAKRWPAEHYAAVAEAKIRAGWQVWLFGSKND

HPGGEEIRQRLIPGLREESFNLAGETSLAEAIDLMSCAGAVVSNDSGLMHVAAALDRP

LVGVYGSTSPQFTPPLADRVEIVRLGLECSPCFERTCRFGHYNCLRELPPGLVLQALE
                    RLVGDPAEVAG"
BASE COUNT      148 a    348 c    364 g    178 t
ORIGIN
        1 atgagaattc tgatcgtagg tccctcctgg gtggggaca tggtgatggc gcagaccctg
       61 ttccagtgtc tgcgccagcg gcatcccgag tgcgtgatcg acgtgctggc gcccgagtgg
      121 agccgaccga tcctcgagcg catgcccgag gtgcgccagg ccctgagctt cccgctcggc
      181 cacggggtga tggacgtcgc cacacggcgc cggatcggac gcggcctgcg cggtcagtac
      241 gagcaggcga tcctgctgcc caactcgctg aagtcggcgc tggtgccctg gttcgccgga
      301 ataccgaagc gtaccggctg gcgcggcgag atgcgctacg gctgctcaa tgacatccgc
      361 aagctcgaca agcagcgcta tccgctgatg atcgaacgct tcatggccct ggccttcgag
      421 ccgggcgtgg agttgccgaa gccctatccg cagccgcgcc tgcggatcga cgacggcagc
      481 cgccaggcgg cgctcgacaa gttcgccctg agcctggacc gcccggtgct ggcgctctgt
      541 cccggcgccg agttcggcga ggccaagcgc tggccggcgg aacactacgc cgcggtcgcc
      601 gaggcgaaga tccgtgccgg ctgcaggtc tggctgttcg gctcgaagaa cgaccatccc
      661 ggtggagagg agattcgcca gcgcctgatt ccggggttgc gcgaggagtc cttcaatctt
      721 gccggggaga cttcgctggc cgaggccatc gacctgatgt cctgcgctgg cgcggtggtg
      781 tccaacgatt ccggcctgat gcacgtggcg gccgcgctgg atcgcccgct ggtgggcgtc
      841 tatggctcca cctcgccgca gttcaccccg ccgctggcgg accgggtgga gatcgtccgc
      901 ctcggtctcg agtgcagccc gtgcttcgag cgcacctgtc gcttcggcca ctacaattgc
      961 ctccgcgagc tgccgcctgg cctggtattg caagccctgg agcggctggt cggcgaccct
     1021 gccgaggtcg ccggatga
//
```

FIGURE 7

```
FEATURES             Location/Qualifiers
     source          1..1068
                     /organism="Pseudomonas aeruginosa"
                     /strain="PAO1"
                     /db_xref="taxon:287"
                     /map="0.3 - 6.6 minutes on the 75 minute linkage map"
     gene            1..1068
                     /gene="rfaC"
     CDS             1..1068
                     /gene="rfaC"
                     /function="adds first heptose onto Kdo of inner core"
                     /function="involved in lipopolysaccharide inner core
                     biosynthesis"
                     /note="RfaC"
                     /codon_start=1
                     /transl_table=11
                     /product="heptosyl transferase I"
                     /db_xref="PID:g1916628"

/translation="MRVLLVKTSSLGDVIHTLPALTDAARAIPGIQFDWVVEEGFAEI
                     PAWHPAVARVIPVAIRRWRKNLWQTLRNGEWRRFKQRLKEVDYDLVIDAQGLLKSAWL
                     TRYVGKTPVAGLDRDSAREPLASRFYRRAYPVAWGQHAVERTRQLFAQALDYPLPESV
                     GEYGLDREQLADADPGAPYLVFLHGTTWVTKHWPEAYWRELAERMCERGWSVRLPWGS
                     AAERERAGRLAAGLENAAVLPRLSLAGMAKVLAGARACVAVDTGLGHLAAALDVPTLS
                     LFGPTNPGFTGAYGRSQVHLGSDFPCAPCLKKTCTYQPTEEDRKLFDLKREQPLCFTR
                     LNPQRVATQLEAMLLAPETLR"
BASE COUNT         155 a      363 c      373 g      177 t
ORIGIN
        1 atgagggtgc tgctggtcaa gacctcgtcc ctcggcgacg tgatccacac cctgccggcg
       61 cttaccgacg ccgcccgggc gattcccggc atccagttcg actgggtggt ggaggaaggt
      121 ttcgccgaga ttcccgcctg gcatccggcg gtggcgcggg tgatcccggt ggcgatccgg
      181 cgctggcgca agaacctctg gcagaccctg cgcaacggcg aatggcggcg cttcaagcag
      241 cgcctgaagg aagtcgacta tgacctggtg atcgacgccc aggggctgct gaagagtgcc
      301 tggctgaccc gctacgtggg caagacgccg gtcgccggtc tcgatcgcga ctcggcgcgc
      361 gagccgctcg ccagccgctt ctatcgccgt gcctatccgg tcgcctgggg acagcatgcg
      421 gtggagcgca cgcgccagtt gttcgcccag gcgctggact acccgttgcc cgagtcggtc
      481 ggtgaatatg gcctggaccg cgagcagttg gccgacgccg accctggcgc gccgtacctg
      541 gtgttcctgc acggtactac ctgggtcacc aagcattggc cggaagccta ctggcgcgaa
      601 ctggccgagc gcatgtgcga gcgcggctgg tcggtgcgcc tgccctgggg cagcgccgcc
      661 gagcgggagc gggccggacg cctggcggcg gggttggaaa atgccgcggt actccccaga
      721 ttatccctgg ccggcatggc caaggtgctt gccggcgcgc gcgcctgcgt ggcggtggat
      781 accggcctcg gtcacctggc ggcggcgctg gacgtgccga cgctgtcgct gttcggcccg
      841 accaatcctg gcttcaccgg cgcctacggg cgttcccagg tccacctggg cagcgacttc
      901 ccctgtgcgc cgtgcctgaa aaagacttgt acctaccagc cgaccgaaga ggatcgcaaa
      961 ctgttcgatc tcaagcgtga gcagccgctg tgcttcaccc ggctgaatcc cagcgcgtg
     1021 gccacccagc tggaggccat gctgctggcc ccggagaccc tccgatga
//
```

FIGURE 8

*Pseudomonas aeruginosa* waaG

ATGACCCTGGCGTTCATCCTCTACAAATACTTCCCCTTCGGCGGCCTGCAGCGTGACTTCATGC
GCATCGCCCTGGAATGCCAGCGGCGCGGGCACGACATCCGCGTCTATACGCTGATCTGGGAGGG
CGACGTGCCGGACGGCTTCGAAGTGCTGGTGGCCCCGGTGCGCTCGATCTTCAACCACCGGCGC
AACGAGAAGTTCACCGCGTGGGTCCGCGCCGACCTGGACAGGCGCCCGGTGCAGCGGGTGATCG
GCTTCAACAAGATGCCCGGACTGGATGTCTACTACGCCGCCGACGCCTGTTTCGAGGAAAAGGC
CCAGACCTTGCGCAACCCGCTGTACCGCCAGTGGGGCCGCTACCGCCACTTCGCCGGCTACGAA
CGGGCAGTGTTCGACCCGGCCTCGAAGACCGAGATCCTGATGATCTCCGAGGTGCAGCAGCCGC
TCTTCGTCAAGCACTACGGCACCCAGGCCGAGCGTTTCCATCTGCTGCCGCCGGGGATCAGTCA
GGATCGCCGGGCGCCGGCCAACGCCGCGGACGTGCGTGCGGAATTCCGCCGCGAGTTCGGCCTG
GAGGAGGACGACCTGCTGCTGGTGCAGATCGGTTCCGGCTTCAAGACCAAGGGCCTGGATCGCA
GCCTGAAGGCGCTGTCCGCGCTGCCCAAGGCGTTGCGCAGGCGTACCCGGCTGATCGCCATCGG
CCAGGACGATCCCAAGCCGTTCCTGCTACAGATCGCCGCCCTCGGTCTCAACGACCAGGTACAG
ATCCTCAAGGGGCGCAGCGATATCCCGCGCTTCCTGCTCGGCGCCGACCTGCTGATCCACCCGG
CCTACAACGAGAACACCGGTACGGTGCTGCTGGAGGCGCTGGTCTCCGGCCTGCCGGTGTTGGT
GACCGATGTCTGCGGCTACGCCTACTACATCGCCGAGGCCGACGCCGGGCGGGTGCTGCCGAGT
CCCTTCGAGCAGGACAGTCTCAACCGCCTGCTCGCGGAAATGCTGGAGGACGCTCCGGCGCGCG
CCGCCTGGTCGCGCAATGGGCTGGCCTACGCCGATCACGCCGACCTCTACAGCATGCCGCAGCG
CGCCGCCGACCTGATCCTCGGGGAGGCCTCATGA

FIGURE 9

*Pseudomonas aeruginosa* WaaG

MTLAFILYKYFPFGGLQRDFMRIALECQRRGHDIRVYTLIWEGDVPDGFEVLVAPV
RSIFNHRRNEKFTAWVRADLDRRPVQRVIGFNKMPGLDVYYAADACFEEKAQTLR
NPLYRQWGRYRHFAGYERAVFDPASKTEILMISEVQQPLFVKHYGTQAERFHLLP
PGISQDRRAPANAADVRAEFRREFGLEEDDLLLVQIGSGFKTKGLDRSLKALSALP
KALRRRTRLIAIGQDDPKPFLLQIAALGLNDQVQILKGRSDIPRFLLGADLLIHPAY
NENTGTVLLEALVSGLPVLVTDVCGYAYYIAEADAGRVLPSPFEQDSLNRLLAEML
EDAPARAAWSRNGLAYADHADLYSMPQRAADLILGEAS

FIGURE 10

```
WaaG_Pa      MTLAFILYKYFPFGGLQRDFMRIALECQRRGHDIRVYTLIWEGDVPDGFE      50
WaaG_Ec      MIVAFCLYKYFPFGGLQRDFMRIASTVAARGHHVRVYTQSWEGDCPKAFE      50
             * .** *****************    *** .****  **** *  **

WaaG_Pa      VLVAPVRSIFNHRRNEKFTAWVRADLDRRPVQRVIGFNKMPGLDVYYAAD      100
WaaG_Ec      LIQVPVKSHTNHGRNAEYYAWVQNHLKEHPADRVVGFNKMPGLDVYFAAD      100
              **.*  ** **  .***    *   * **.************.***

WaaG_Pa      ACFEEKAQTLRNPLYRQWGRYRHFAGYERAVFDPASKTEILMISEVQQPL      150
WaaG_Ec      VCYAEKVAQEKGFLYRLTSRYRHYAAFERATFEQGKSTKLMMLTDKQIAD      150
             *. **    .  ***  ****.* .*** *.   * ..*... *

WaaG_Pa      FVKHYGTQAERFHLLPPGISQDRRAPANAADVRAEFRREFGLEEDDLLLV      200
WaaG_Ec      FQKHYQTEPERFQILPPGIYPDRKYSEQIPNSREIYRQKNGIKEQQNLLL      200
             * *** *  *** .***** **.       *  .*   *.  *   **.

WaaG_Pa      QIGSGFKTKGLDRSLKALSALPKALRRRTRLIAIGQDDPKPFLLQIAALG      250
WaaG_Ec      QVGSDFGRKGVDRSIEALASLPESLRHNTLLFVVGQDKPRKFEALAEKLG      250
             *.** *  * ***. **.**  .**  .**  * *** *.*  **   **

WaaG_Pa      LNDQVQILKGRSDIPRFLLGADLLIHPAYNENTGTVLLEALVSGLPVLVT      300
WaaG_Ec      VRSNVHFFSGRNDVSELMAAADLLLHPAYQEAAGIVLLEAITAGLPVLTT      300
              . .*    ** *.    ****.****.* .* *****. .***** *

WaaG_Pa      DVCGYAYYIAEADAGRVLPSPFEQDSLNRLLAEMLEDAPARAAWSRNGLA      350
WaaG_Ec      AVCGYAHYIADANCGTVIAEPFSQEQLNEVLRKALTQSPLRMAWAENARH      350
              ***** ***.*  * * *. ** .* *  * *    .* .*  **. *

WaaG_Pa      YADHADLYSMPQRAADLILGE-AS      373
WaaG_Ec      YADTQDLYSLPEKAADIITGGLDG      374
             ***  ****.* .***.* *

Pseudomonas aeruginosa (Pa) vs Escherichia coli (Ec)
Identity : 187 (50.13%)
```

PROTEINS INVOLVED IN THE SYNTHESIS AND ASSEMBLY OF CORE LIPOPOLYSACCHARIDE OF *PSEUDOMONAS AERUGINOSA*

This is a continuation application of International Application No. PCT/CA98/00395 with an International filing date of May 1, 1998, now abandoned, which claims priority from U.S. Provisional Application No. 60/045,418 filed May 2, 1997 and U.S. Provisional Application No. 60/046,149 filed May 9, 1997.

FIELD OF THE INVENTION

The invention relates to novel nucleic acid molecules encoding proteins involved in the synthesis and assembly of core lipopolysaccharide of *P. aeruginosa,* the novel proteins encoded by the nucleic acid molecules; and, uses of the proteins and nucleic acid molecules.

BACKGROUND OF THE INVENTION

Gram negative bacterial infections account for a significant number of hospital-acquired infections. The majority of hospital-acquired infections are due to gram negative organisms such as *Escherichia coli, Klebsiella pneumoniae* and *Pseudomonas aeruginosa.* Gram negative infections are particularly common among individuals receiving chemotherapy, and immunocompromised individuals. These individuals often develop resistance to antibiotics over the long course of the infection making conventional treatment difficult.

Many virulence factors have been identified in the pathogenesis of gram negative bacteria, including lipopolysaccharide. The lipolypolysaccharide of gram negative bacteria is composed of O-antigen, usually tri- or tetrasaccharide repeating units, which is immunodominant and responsible for serotype specificity. The O-antigen is attached to a core oligosaccharide composed of hexoses and octoses, which is itself attached to lipid A (endotoxin) embedded in the cell membrane. The core lipopolysaccharide structure, particularly the inner core region, appears to be widely shared among diverse gram negative bacterial genera.

Genes involved in the biosynthesis of core oligosaccharides have been cloned and characterized from several bacterial species, including *Escherichia coli,* ( Parker et al., J. Bacteriol. 174, 93–0934, 1992; Genbank Accession No. M80599, M86935), *Salmonella typhimurium* (Klena et al., J. Bacteriol. 175(5) 1524–1527, 1993; Genbank Accession No. S56361), and *Haemophilus influenzae* (High N. J et al., Mol. Microbiol. 9(6) 1275–1282, 1993; Genbank Accession No. L19441).

SUMMARY OF THE INVENTION

The present inventors have characterized a gene cluster involved in the synthesis and assembly of core lipopolysaccharide of *P. aeruginosa.* The gene cluster is also known as and referred to herein as the waa (or rfa) gene cluster, and the proteins encoded by the genes are referred to herein as Waa (or Rfa) proteins.

The waa gene cluster contains the genes waaF, waaC, waaG and waaP. The arrangement of the genes in the waa gene cluster is shown in FIG. 2, and their role in the biosynthesis of the lipopolysaccharide core structure of *P. aeuroginosa* serotypes O5 and O6 is shown in FIG. 1.

The identification and sequencing of the genes and proteins in the waa gene cluster permits the identification of substances which affect core lipopolysaccharide synthesis or assembly in *P. aeruginosa.* These substances may be useful in inhibiting core lipopolysaccharide synthesis or assembly rendering the microorganisms more susceptible to attack by host defence mechanisms.

Broadly stated the present invention relates to an isolated *P. aeruginosa* waa gene cluster comprising the genes waaF, waaC, waaG, and waaP involved in the synthesis, and assembly of core lipopolysaccharide in *P. aeruginosa.*

The present invention also relates to nucleic acid molecules encoding WaaF, WaaC, WaaG and WaaP proteins.

The invention also contemplates a nucleic acid molecule comprising a sequence encoding a truncation of a protein of the invention, an analog, or a homolog of a protein of the invention, or a truncation thereof.

The nucleic acid molecules of the invention may be inserted into an appropriate expression vector, i.e. a vector which contains the necessary elements for the transcription and translation of the inserted coding sequence. Accordingly, recombinant expression vectors adapted for transformation of a host cell may be constructed which comprise a nucleic acid molecule of the invention and one or more transcription and translation elements operatively linked to the nucleic acid molecule.

The recombinant expression vector may be used to prepare transformed host cells expressing a protein of the invention. Therefore, the invention further provides host cells containing a recombinant molecule of the invention.

The invention further provides a method for preparing a protein of the invention utilizing the purified and isolated nudeic acid molecules of the invention. In an embodiment a method for preparing a protein of the invention is provided comprising (a) transferring a recombinant expression vector of the invention into a host cell; (b) selecting transformed host cells from untransformed host cells; (c) culturing a selected transformed host cell under conditions which allow expression of the protein; and (d) isolating the protein.

The invention further broadly contemplates an isolated protein characterized in that it has part or all of the primary structural conformation (ie. continuous sequence of amino acid residues) of a novel protein encoded by a gene of the waa gene cluster of the invention. In an embodiment of the invention, a purified protein is provided which has the amino acid sequence as shown in FIG. 4, FIG. 6, FIG. 7, or FIG. 9. The invention also includes truncations of the protein and analogs, homologs, and isoforms of the protein and truncations thereof.

The proteins of the invention may be conjugated with other molecules, such as proteins, to prepare fusion proteins. This may be accomplished, for example, by the synthesis of N-terminal or C-terminal fusion proteins.

The nucleic acid molecules of the invention allow those skilled in the art to construct nucleotide probes for use in the detection of nucleotide sequences in samples such as biological (e.g clinical specimens), food, or environmental samples. The nucleotide probes may also be used to detect nucleotide sequences that encode proteins related to or analogous to the proteins of the invention.

Accordingly, the invention provides a method for detecting the presence of a nudeic acid molecule having a sequence encoding a protein of the invention, comprising contacting the sample with a nucleotide probe which hybridizes with the nucleic acid molecule, to form a hybridization product under conditions which permit the formation of the hybridization product, and assaying for the hybridization product.

The invention further provides a kit for detecting the presence of a nucleic acid molecule having a sequence encoding a protein of the invention, comprising a nudeotide probe which hybridizes with the nucleic acid molecule, reagents required for hybridization of the nucleotide probe with the nucleic acid molecule, and directions for its use.

The nucleic acid molecules of the invention also permit the identification and isolation, or synthesis, of nucleotide sequences which may be used as primers to amplify a nucleic acid molecule of the invention, for example in the polymerase chain reaction (P CR).

Accordingly, the invention relates to a method of determining the presence of a nucleic acid molecule having a sequence encoding a protein of the invention in a sample, comprising treating the sample with primers which are capable of amplifying the nucleic acid molecule in an amplification reaction, preferably in a polymerase chain reaction, to form amplified sequences, under conditions which permit the formation of amplified sequences, and, assaying for amplified sequences.

The invention further relates to a kit for determining the presence of a nucleic acid molecule having a sequence encoding a protein of the invention in a sample, comprising primers which are capable of amplifying the nucleic acid molecule in an amplification reaction, preferably a polymerase chain reaction, to form amplified sequences, reagents required for amplifying the nudeic acid molecule thereof in the amplification reaction, means for assaying the amplified sequences, and directions for its use.

The invention also relates to an antibody specific for an epitope of a protein of the invention or a part thereof, and methods for preparing the antibodies. Antibodies specific for a protein encoded by a waa gene of the invention can be used to detect *P. aeruginosa* of all serotypes in a sample.

Therefore, the invention also relates to a method for detecting *P. aeruginosa* of all serotypes in a sample comprising contacting a sample with an antibody specific for an epitope of a protein encoded by a waa gene of the invention which antibody is capable of being detected after it becomes bound to a protein in the sample, and assaying for antibody bound to protein in the sample, or unreacted antibody.

A kit for detecting *P. aeruginosa* serotypes in a sample comprising an antibody of the invention, preferably a monoclonal antibody and directions for its use is also provided. The kit may also contain reagents which are required for binding of the antibody to the protein in the sample.

As discussed above, the identification and sequencing of genes in the waa gene cluster in *P. aeruginosa* permits the identification of substances which affect the activity of the proteins encoded by the genes in the duster, or the expression of the proteins, thereby affecting core lipopolysaccharide synthesis or assembly. These substances may be useful in rendering the microorganisms more susceptible to attack by host defence mechanisms. Accordingly, the invention provides a method for assaying for a substance that affects one or both of *P. aeruginosa* core lipopolysaccharide synthesis or assembly comprising mixing a protein or nucleic acid molecule of the invention with a test substance which is suspected of affecting *P. aeruginosa* core lipopolysaccharide synthesis or assembly, and determining the effect of the substance by comparing to a control.

Substances that inhibit the synthesis or assembly of core lipopolysaccharides may be useful in treating or preventing bacterial infections by rendering the bacteria more susceptible to attack by host defense mechanisms. Accordingly, the present invention also provides a method for preventing or treating the bacterial infection comprising administering an effective amount of a substance that inhibits the synthesis or assembly of core lipopolysaccharides. In one embodiment, the substance inhibits the activity of one or more Waa proteins of the invention. Such substances include antibodies to the Waa proteins or other substances that bind the Waa proteins. In another embodiment, the substances may inhibit the expression of one or more waa genes. Such substances include antisense oligonucleotides that bind one or more waa genes or other substances that bind the nucleic acid sequences of the invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF DRAWINGS

The invention will now be described in relation to the drawings:

FIG. 3 (and SEQ.ID.NO.:1) shows a nucleic acid sequence encoding a WaaP protein of the invention;

FIG. 4 (and SEQ.ID.NO.:2) shows an amino acid sequence of the WaaP protein of the invention;

FIG. 5 shows an alignment of an amino acid sequence of WaaP of *P. aeruginosa* serotype O5 and an amino acid sequence of WaaP of *E. coli*;

FIG. 6 shows a nucleic acid sequence of waaF (SEQ.ID.NO.: 3) and an amino acid sequence of a WaaF protein (SEQ.ID.NO.:4) of the invention;

FIG. 7 shows a nucleic acid sequence of waaC, (SEQ.ID.NO.:5) and an amino acid sequence of the WaaC protein (SEQ.ID.NO.:6) of the invention;

FIG. 8 (and SEQ.ID.NO.:7) shows the nucleic acid sequence encoding an WaaG protein of the invention;

FIG. 9 (and SEQ.ID.NO.:8) shows the amino acid sequence of an WaaG protein of the invention;

FIG. 10 shows the alignment of amino acids of WaaG (*P. aeruginosa*) and WaaG (*E. coli*)

DETAILED DESCRIPTION OF THE INVENTION

The following standard abbreviations for the amino acid residues are used throughout the specification: A, Ala—alanine; C, Cys—cysteine; D, Asp—aspartic acid; E, Glu—glutamic acid; F, Phe—phenylalanine; G, Gly—glycine; H, His—histidine; I, Ile—isoleucine; K, Lys—lysine; L, Leu—leucine; M, Met—methionine; N, Asn—asparagine; P, Pro—proline; Q, Gln—glutamine; R, Arg—arginine; S, Ser—serine; T, Thr—threonine; V, Val—valine; W, Trp—tryptophan; Y, Tyr—tyrosine; and p.Y., P.Tyr—phosphotyrosine.

I. Nucleic Acid Molecules of the Invention

As hereinbefore mentioned, the present invention relates to an isolated *P. aeruginosa* waa gene cluster containing genes involved in the synthesis and assembly of core lipopolysaccharide in *P. aeruginosa*. The present invention also relates to the isolated genes which comprise the cluster.

The term "isolated" refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

The *P. aeruginosa* B-band gene cluster comprises the following genes: waaF, waaC, waaG, and waaP involved in the synthesis, and assembly of core lipopolysaccharide in *P. aeruginosa*.

Figure 1:
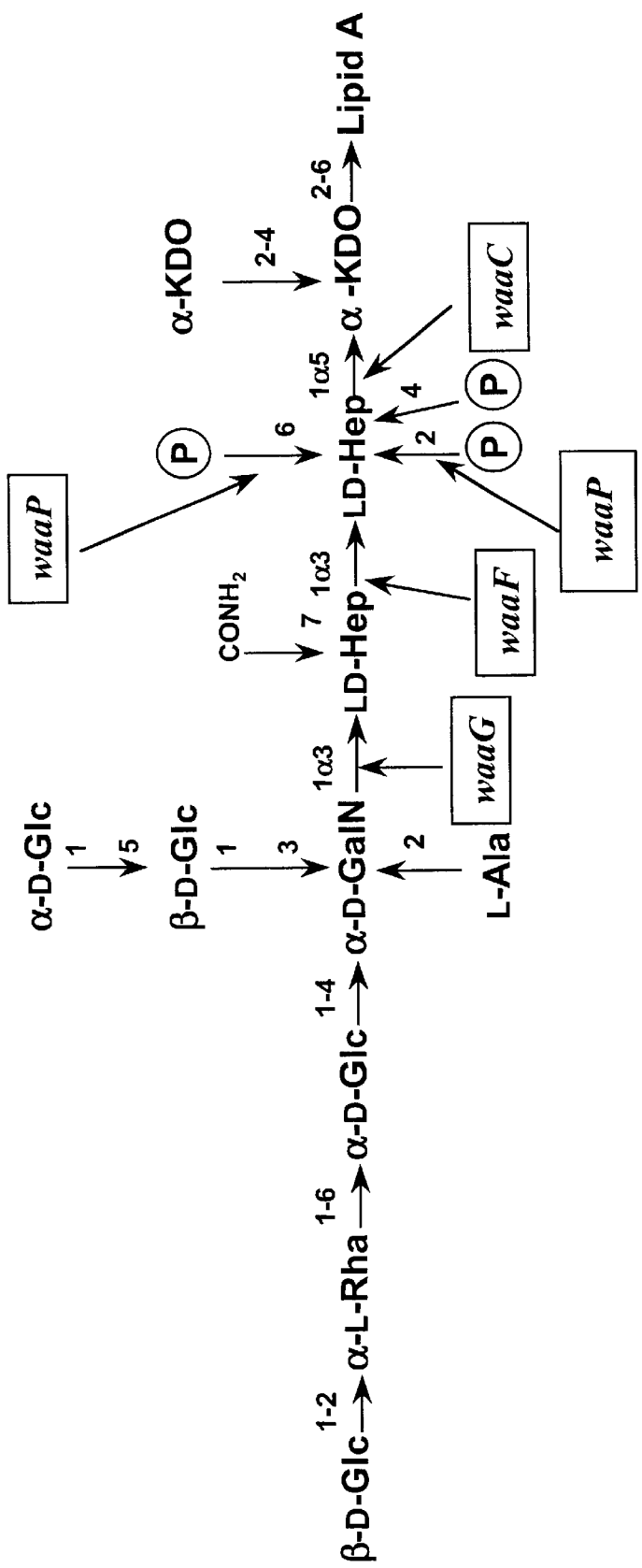
FIG. 1 shows the role of the waa genes in the biosynthesis of the lipopolysaccharide core of *P. aeruginosa*.
Figure 2:
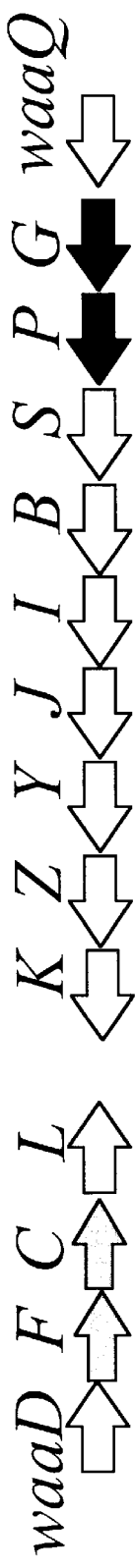
FIG. 2 shows the organization of the *P. aeruginosa* PAO1 waa gene cluster.

The genes preferably have the organization as shown in FIG. 2. The gene waaP encodes a protein that phosphorylates an inner-core heptose residue of lipopolysaccharide while waaG encodes a transferase which link the galactosamine residue of the outer-core to the second inner-core heptose residue.

The invention provides nucleic acid molecules encoding the WaaF, WaaC, WaaG and WaaP proteins involved in *P. aeruginosa* core lipopolysaccharide synthesis and assembly. In addition, nucleic acid molecules are provided which contain sequences encoding two or more of the following proteins WaaF, WaaC, WaaG and WaaP.

In an embodiment of the invention, an isolated nucleic acid molecule is provided having a sequence which encodes a protein having an amino acid sequence as shown in FIG. 4, FIG. 6, FIG. 7, or FIG. 9.

Preferably, the purified and isolated nucleic acid molecule comprises (a) a nucleic acid sequence as shown in FIG. 3, FIG. 6, FIG. 7, or FIG. 8, wherein T can also be U;

(b) nucleic acid sequences complementary to (a);

(c) nucleic add sequences which are homologous to (a) or (b);

(d) a fragment of (a) to (c) that is at least 15 bases, preferably 20 to 30 bases, and which will hybridize to (a) to (c) under stringent hybridization conditions; or (e) a nucleic acid molecule differing from any of the nucleic acids of (a) to (c) in codon sequences due to the degeneracy of the genetic code.

Specific embodiments of the nucleic acid molecule of the invention include the following:

1. An isolated nucleic acid molecule characterized by having a sequence encoding a WaaP protein of *P. aeruginosa* which phosphorylates an inner core heptose residue of lipopolysaccharide. The nucleic acid molecule preferably encodes WaaP having the amino acid sequence as shown in FIG. 4 and most preferably comprises the nucleic acid sequence as shown in FIG. 3.

2. An isolated nucleic acid molecule characterized by having a sequence encoding a WaaG protein of *P. aeruginosa* which is a transferase which link the galactosamine residue of the outer-core to the second inner-core heptose residue. The nucleic acid molecule preferably encodes WaaG having the amino acid sequence as shown in FIG. 9, and most preferably comprises the nucleic acid sequence as shown in FIG. 8.

3. An isolated nucleic acid molecule characterized by having a sequence encoding a WaaF protein of *P. aeruginosa* that is a heptosyl transferase II. The nucleic acid molecule preferably encodes WaaF having the amino acid sequence as shown in FIG. 6, and most preferably comprises the nudeic acid sequence as shown in FIG. 6.

4. An isolated nucleic acid molecule characterized by having a sequence encoding a WaaC protein of *P. aeruginosa* that is a heptosyl transferase I. The nucleic acid molecule preferably encodes WaaC having the amino acid sequence as shown in FIG. 7, and most preferably comprises the nucleic acid sequence as shown in FIG. 7.

In an embodiment of the invention, the nucleic acid molecule contains two genes from the waa gene cluster of the invention, preferably two genes which are adjacent in the gene cluster. For example, may contain a nucleic acid sequence of waaG and waaP.

It will be appreciated that the invention includes nucleic acid molecules encoding truncations of the proteins of the invention, and analogs and homologs of the proteins of the invention and truncations thereof, as described below. It will further be appreciated that variant forms of the nucleic acid molecules of the invention which arise by alternative splicing of an mRNA corresponding to a cDNA of the invention are encompassed by the invention.

Further, it will be appreciated that the invention includes nucleic acid molecules comprising nucleic acid sequences having substantial sequence homology with the nucleic acid sequences as shown in FIG. 3, FIG. 6, FIG. 7, or FIG. 8, and fragments thereof. The term "sequences having substantial sequence homology" means those nucleic acid sequences which have slight or inconsequential sequence variations from these sequences, i.e. the sequences function in substantially the same manner to produce functionally equivalent proteins. The variations may be attributable to local mutations or structural modifications. Generally, nucleic acid sequences with at least 55%, preferably at least 70%, most preferably at least 95% identity are contemplated within the present invention.

Nucleic acid sequences having substantial homology with the nucleic acid molecule encoding WaaP include nucleic acid sequences having at least 54%, preferably at least 70%, most preferably 80 to 95% identity with the nucleic acid sequence as shown in FIG. 3. By way of example, it is expected that a sequence having 80% sequence homology with the DNA sequence encoding WaaP of the invention will provide a functional WaaP protein.

Nucleic acid sequences having substantial homology with the nucleic acid molecule encoding WaaG include nucleic acid sequences having at least 48%, preferably at least 70%, most preferably 80 to 95% identity with the nucleic acid sequence as shown in FIG. 8. By way of example, it is expected that a sequence having 80% sequence homology with the DNA sequence encoding WaaG of the invention will provide a functional WaaP protein.

Another aspect of the invention provides a nucleic acid molecule, and fragments thereof having at least 15 bases, which hybridizes to the nucleic acid molecules of the invention under hybridization conditions, preferably stringent hybridization conditions. Appropriate stringency conditions which promote DNA hybridization are known to those skilled in the art, or may be found in Current Protocols in Molecular Biology, John Wiley & Sons, N.Y. (1989), 6.3.1–6.3.6. For example, the following may be employed: 6.0×sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

Isolated and purified nucleic acid molecules having sequences which differ from the nucleic acid sequence shown in FIG. 3, FIG. 6, FIG. 7, or FIG. 8, due to degeneracy in the genetic code are also within the scope of the invention. Such nucleic acids encode functionally equivalent proteins but differ in sequence from the above mentioned sequences due to degeneracy in the genetic code.

An isolated nucleic acid molecule of the invention which comprises DNA can be isolated by preparing a labelled nudeic acid probe based on all or part of the nucleic acid sequences as shown in FIG. 3, FIG. 6, FIG. 7, or FIG. 8, and using this labelled nucleic acid probe to screen an appropriate DNA library (e.g. a cDNA or genomic DNA library). For example, a whole genomic library isolated from a microorganism, such as a serotype of P. aeruginosa, can be used to isolate a DNA encoding a novel protein of the invention by screening the library with the labelled probe using standard techniques. Nucleic acids isolated by screening of a cDNA or genomic DNA library can be sequenced by standard techniques.

An isolated nucleic acid molecule of the invention which is DNA can also be isolated by selectively amplifying a nucleic acid encoding a novel protein of the invention using the polymerase chain reaction (PCR) methods and cDNA or genomic DNA. It is possible to design synthetic oligonucleotide primers from the nucleic acid molecules containing the nucleic acid sequence as shown in FIG. 3, FIG. 6, FIG. 7, or FIG. 8, for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes a novel protein of the invention. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g.; Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a novel protein of the invention may be accomplished by expressing the cDNA in an appropriate host cell by standard techniques, and testing the activity of the protein using the methods as described herein. For example, the activity of a putative WaaG protein may be tested by mixing with an appropriate acceptor and donor and assaying for transferase activity. A cDNA having the activity of a novel protein of the invention so isolated can be sequenced by standard techniques, such as dideoxynucleotide chain termination or Maxam-Gilbert chemical sequencing, to determine the nucleic acid sequence and the predicted amino acid sequence of the encoded protein.

The initiation codon and untranslated sequences of the nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably one or more of the nucleic acid sequences shown in FIG. 3, FIG. 6, FIG. 7, or FIG. 8 may be inverted relative to their normal presentation for transcription to produce antisense nucleic acid molecules.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein.

II. Proteins of the Invention

The invention further broadly contemplates an isolated protein characterized in that it has part or all of the primary structural conformation (ie. continuous sequence of amino acid residues) of a protein encoded by a gene of the waa gene cluster of the invention. In an embodiment of the invention, an isolated protein is provided which has the amino acid sequence as shown in FIG. 4 (WaaP), FIG. 9 (WaaG), FIG. 6 (WaaF), or FIG. 7 (WaaC).

Specific embodiments of the invention include the following:

1. An isolated WaaG protein of P. aeruginosa which is a transferase which link the galactosamine residue of the outer-core to the second inner-core heptose residue, having the amino acid sequence as shown in FIG. 9.

2. An isolated WaaP protein of P. aeruginosa which phosphorylates an inner-core heptose residue of lipolysaccharide, having the amino acid sequence as shown in FIG. 4.

3. An isolated WaaF protein of P. aeruginosa which is a heptosyl transferase II, having the amino acid sequence as shown in FIG. 6.

4. An isolated WaaC protein of P. aeruginosa which is a heptosyl transferase I, having the amino acid sequence as shown in FIG. 7.

Within the context of the present invention, a protein of the invention may include various structural forms of the primary protein which retain biological activity. For example, a protein of the invention may be in the form of acidic or basic salts or in neutral form. In addition, individual amino acid residues may be modified by oxidation or reduction.

In addition to the full length amino acid sequences (FIGS. 4, 6, 7, or 9), the proteins of the present invention may also include truncations of the proteins, and analogs, and homologs of the proteins and truncations thereof as described herein. Truncated proteins may comprise peptides of at least fifteen amino acid residues.

The proteins of the invention may also include analogs of the proteins having the amino acid sequences shown in FIGS. 4, 6, 7, or 9 and/or truncations thereof as described herein, which may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequences shown in FIGS. 4, 6, 7, or 9. Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Deletions may consist of the removal of one or more amino acids, or discrete portions from the amino acid sequences shown in FIGS. 4, 6, 7, or 9. The deleted amino acids may or may not be contiguous. The lower limit length of the resulting analog with a deletion mutation is about 10 amino acids.

Analogs of a protein of the invention may be prepared by introducing mutations in the nucleotide sequence encoding the protein. Mutations in nudeotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequences shown in FIGS. 4, 6, 7, or 9 and/or truncations thereof as described herein. Such homologs are proteins whose amino acid sequences are comprised of amino acid sequences that hybridize under stringent hybridization conditions (see discussion of stringent hybridization conditions herein) with a probe used to obtain a protein of the invention. Homologs of a protein of the invention will have the same regions which are characteristic of the protein. Generally, the invention contemplates Waa proteins having at least 55%, preferably at least 70%, most preferably at least 80 to 95% identity.

An amino acid alignment for the WaaP protein is shown in FIG. 4. It will be appreciated that the invention includes WaaP proteins having at least 54% identity. In addition, an amino acid alignment for the WaaG protein is shown in FIG. 10. It will be appreciated that the invention includes WaaG proteins having at least 48% identity.

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein (see below) to produce fusion proteins. Additionally, immunogenic portions of a protein of the invention are within the scope of the invention.

The proteins of the invention (including truncations, analogs, etc.) may be prepared using recombinant DNA methods. Accordingly, the nucleic acid molecules of the present invention having a sequence which encodes a protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary. regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence as shown in FIGS. 3, 6, 7, or 8. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as E. coli, insect cells (using baculovirus), yeast cells or mammalian cells. Other suitable host cells can be found in Goeddel, Gene Expression Technology: Methods in Enzymology 185, Academic Press, San Diego, Calif. (1991).

More particularly, bacterial host cells suitable for carrying out the present invention include E. coli, as well as many other bacterial species well known to one of ordinary skill in the art. Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., Nature 275:615, 1978), the trp promoter (Nichols and Yanofsky, Meth in Enzymology 101:155, 1983) and the tac promoter (Russell et al., Gene 20: 231, 1982). Representative selectable markers include various antibiotic resistance markers such as the kanamycin or ampicillin resistance genes. Suitable expression vectors include but are not limited to bacteriophages such as lambda derivatives or plasmids such as pBR322 (see Bolivar et al., Gene 2:9S, 1977), the pUC plasmids pUC18, pUC19, pUC118, pUC119 (see Messing, Meth in Enzymology 101:20–77, 1983 and Vieira and Messing, Gene 19:259–268, 1982), and pNH8A, pNH16a, pNH18a, and Bluescript M13 (Stratagene, La Jolla, Calif.).

Yeast and fungi host cells suitable for carrying out the present invention include, but are not limited to *Saccharomyces cerivisae*, the genera Pichia or Kluyveromyces and various species of the genus Aspergillus. Examples of vectors for expression in yeast *S. cerivisae* include pYepSe1 (Baldari. et al., (1987) Embo J. 6:229–234), pMFa (Kurjan and Herskowitz, (1982) Cell 30:933–943), pJRY88 (Schultz et al., (1987) Gene 54:113–123), and pYES2 (Invitrogen Corporation, San Diego, Calif.). Protocols for the transformation of yeast and fungi are well known to those of ordinary skill in the art.(see Hinnen et al., PNAS USA 75:1929, 1978; Itoh et al., J. Bacteriology 153:163, 1983, and Cullen et al. (Bio/Technology 5:369, 1987).

The proteins of the invention may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

III. Applications

A. Diagnostic Applications

The nucleic acid molecules of the invention, allow those skilled in the art to construct nucleotide probes for use in the detection of nucleotide sequences in a sample. A nucleotide probe may be labelled with a detectable marker such as a radioactive label which provides for an adequate signal and has sufficient half life such as $^{32}P$, $^{3}H$, $^{14}C$ or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

The nucleotide probes may be used to detect genes that encode proteins related to or analogous to proteins of the invention.

Accordingly, the present invention also relates to a method of detecting the presence of nucleic acid molecules encoding a protein of the invention in a sample comprising contacting the sample under hybridization conditions with one or more of nucleotide probes which hybridize to the nucleic acid molecules and are labelled with a detectable marker, and determining the degree of hybridization between the nucleic acid molecule in the sample and the nucleotide probes.

In an embodiment of the invention a method for detecting P. aeruginosa of all serotypes in a sample comprising contacting the sample with a nucleotide sequence encoding WaaF, WaaC, WaaG or WaaP, or a fragment thereof, under conditions which permit the nucleic acid molecule to hybridize with a complementary sequence in the sample to form a hybridization product, and assaying for the hybridization product.

Hybridization conditions which may be used in the methods of the invention are known in the art and are described for example in Sambrook J, Fritch E F, Maniatis T. In: Molecular Cloning, A Laboratory Manual,1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

The nucleic acid molecule of the invention also permits the identification and isolation, or synthesis of nucleotide sequences which may be used as primers to amplify a nucleic acid molecule of the invention, for example in the polymerase chain reaction (PCR) which is discussed in more detail below. The primers may be used to amplify the genomic DNA of other bacterial species known to have LPS. The PCR amplified sequences can be examined to determine the relationship between the various LPS genes.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length.

Primers which may be used in the invention are oligonucleotides i.e. molecules containing two or more deoxyribonucleotides of the nucleic acid molecule of the invention which occur naturally as in a purified restriction endonuclease digest or are produced synthetically using techniques known in the art such as for example phosphotriester and phosphodiester methods (See Good et al Nucl. Acid Res 4:2157, 1977) or automated techniques (See for example, Conolly, B. A. Nucleic Acids Res. 15:15(7): 3131, 1987). The primers are capable of acting as a point of initiation of synthesis when placed under conditions which permit the synthesis of a primer extension product which is complementary to the DNA sequence of the invention i.e. in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl chloride, fluorcein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide fragment thereof, which is to be amplified. Restriction site linkers may also be incorporated into the primers allowing for digestion of the amplified products with the appropriate restriction enzymes facilitating cloning and sequencing of the amplified product.

In an embodiment of the invention a method of determining the presence of a nucleic acid molecule having a sequence encoding a protein of the invention is provided comprising treating the sample with primers which are capable of amplifying the nucleic acid molecule or a predetermined oligonucleotide fragment thereof in a polymerase chain reaction to form amplified sequences, under conditions which permit the formation of amplified sequences and, assaying for amplified sequences.

In a preferred embodiment of the invention, a method for detecting P. aeruginosa in a sample is provided comprising treating the sample with a primer which is capable of amplifying nucleic acid molecules comprising nucleotide sequences encoding WaaF, WaaC, WaaP or WaaG, or a predetermined oligonucleotide fragment thereof, in a polymerase chain reaction to form amplified sequences, under conditions which permit the formation of amplified sequences and, assaying for amplified sequences.

The polymerase chain reaction refers to a process for amplifying a target nucleic acid sequence as generally described in Innis et al, Academic Press, 1990 in Mullis el al., U.S. Pat. No. 4,863,195 and Mullis, U.S. Pat. No. 4,683,202 which are incorporated herein by reference. Conditions for amplifying a nucleic acid template are described in M. A. Innis and D. H. Gelfand, PCR Protocols, A Guide to Methods and Applications M. A. Innis, D. H. Gelfand, J. J. Sninsky and T. J. White eds, pp3–12, Academic Press 1989, which is also incorporated herein by reference.

The amplified products can be isolated and distinguished based on their respective sizes using techniques known in the art. For example, after amplification, the DNA sample can be separated on an agarose gel and visualized, after staining with ethidium bromide, under ultra violet (UV) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers as discussed above. The detectable markers may be analyzed by restriction and electrophoretic separation or other techniques known in the art.

The conditions which may be employed in the methods of the invention using PCR are those which permit hybridization and amplification reactions to proceed in the presence of DNA in a sample and appropriate complementary hybridization primers. Conditions suitable for the polymerase chain reaction are generally known in the art. For example, see M. A. Innis and D. H. Gelfand, PCR Protocols, A guide to Methods and Applications M. A. Innis, D. H. Gelfand, J. J. Sninsky and T. J. White eds, pp3–12, Academic Press 1989, which is incorporated herein by reference. Preferably, the PCR utilizes polymerase obtained from the thermophilic bacterium *Thermus aquatics* (Taq polymerase, GeneAmp Kit, Perkin Elmer Cetus) or other thermostable polymerase may be used to amplify DNA template strands.

It will be appreciated that other techniques such as the Ligase Chain Reaction (LCR) and NASBA may be used to amplify a nucleic acid molecule of the invention (Barney in "PCR Methods and Applications", August 1991, Vol.1(1), page 5, and European Published Application No. 0320308, published Jun. 14, 1989, and U.S. Ser. No. 5,130,238 to Malek).

A protein of the invention can be used to prepare antibodies specific for the protein. Antibodies can be prepared which bind a distinct epitope in an unconserved region of the protein. An unconserved region of the protein is one which does not have substantial sequence homology to other proteins. Alternatively, a region from a well-characterized domain can be used to prepare an antibody to a conserved region of a protein of the invention. Antibodies having specificity for a protein of the invention may also be raised from fusion proteins.

Conventional methods can be used to prepare the antibodies. For example, by using a peptide of a protein of the invention, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495–497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77–96), and screening of combinatorial antibody libraries (Huse et al., Science 246, 1275 (1989)]. Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a protein of the invention.

The term "antibody" as used herein is intended to include fragments thereof which also specifically react with a protein, of the invention, or peptide thereof. Antibodies can be fragmented using conventional techniques and the fragments screened for utility in the same manner as described above. For example, F(ab')$_2$ fragments can be generated by treating antibody with pepsin. The resulting F(ab')$_2$ fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of the genes of the waa cluster of the invention (See, for example, Morrison et al., Proc. Natl Acad. Sci. U.S.A. 81,6851 (1985); Takeda et al., Nature 314, 452 (1985), Cablly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against proteins of the invention may also be generated by screening expression libraries encoding immunoglobulin genes, or portions thereof, expressed in bacteria with peptides produced from the nucleic acid molecules of the present invention. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348, 552–554 (1990)). In an embodiment of the invention, antibodies that bind to an epitope of a protein of the invention are engineered using the procedures described in N. Tout and J. Lam (Clinc. Diagn. Lab. Immunol. Vol. 4(2):147–155, 1997).

The antibodies may be labelled with a detectable marker including various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, I-123, I-125, I131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

The antibodies reactive against proteins of the invention (e.g. enzyme conjugates or labeled derivatives) may be used to detect a protein of the invention in various samples, for example they may be used in any known immunoassays which rely on the binding interaction between an antigenic determinant of a protein of the invention and the antibodies. Examples of such assays are radioimmunoassays, enzyme immunoassays (e.g. ELISA), immunofluorescence, immunoprecipitation, latex agglutination, hemagglutination, and histochemical tests. Thus, the antibodies may be used to identify or quantify the amount of a protein of the invention in a sample in order to diagnose P. aeruginosa infections.

A sample may be tested for the presence or absence of P. aeruginosa by contacting the sample with an antibody specific for an epitope of WaaF, WaaC, WaaP or WaaG, which antibody is capable of being detected after it becomes bound to a WaaF, WaaC, WaaP or WaaG protein or part thereof, in the sample, and assaying for antibody bound to WaaF, WaaC, WaaP or WaaG protein or part thereof, in the sample, or unreacted antibody. A sample may also be tested for the presence or absence of P. aeruginosa, by contacting the sample with an antibody specific for an epitope of a WaaF, WaaC, WaaP or WaaG protein which antibody is capable of being detected after it becomes bound to the protein or part thereof in the sample, and assaying for antibody bound to protein or part thereof in the sample, or unreacted antibody.

In a method of the invention a predetermined amount of a sample or concentrated sample is mixed with antibody or labelled antibody. The amount of antibody used in the process is dependent upon the labelling agent chosen. The resulting protein bound to antibody or labelled antibody may be isolated by conventional isolation techniques, for example, salting out, chromatography, electrophoresis, gel filtration, fractionation, absorption, polyacrylamide gel electrophoresis, agglutination, or combinations thereof.

The sample or antibody may be insolubilized, for example, the sample or antibody can be reacted using known methods with a suitable carrier. Examples of suitable carriers are Sepharose or agarose beads. When an insolubilized sample or antibody is used protein bound to antibody or unreacted antibody is isolated by washing. For example, when the sample is blotted onto a nitrocellulose membrane, the antibody bound to a protein of the invention is separated from the unreacted antibody by washing with a buffer, for example, phosphate buffered saline (PBS) with bovine serum albumin (BSA).

When labelled antibody is used, the presence of P. aeruginosa, can be determined by measuring the amount of labelled antibody bound to a protein of the invention in the sample or of the unreacted labelled antibody. The appropriate method of measuring the labelled material is dependent upon the labelling agent.

When unlabelled antibody is used in the method of the invention, the presence of P. aeruginosa can be determined by measuring the amount of antibody bound to the P. aeruginosa using substances that interact specifically with the antibody to cause agglutination or precipitation. In particular, labelled antibody against an antibody specific for a protein of the invention, can be added to the reaction mixture. The presence of P. aeruginosa can be determined by a suitable method from among the already described techniques depending on the type of labelling agent. The antibody against an antibody specific for a protein of the invention can be prepared and labelled by conventional procedures known in the art which have been described herein. The antibody against an antibody specific for a protein of the invention may be a species specific anti-immunoglobulin antibody or monoclonal antibody, for example, goat anti-rabbit antibody may be used to detect rabbit antibody specific for a protein of the invention.

The reagents suitable for applying the methods of the invention may be packaged into convenient kits providing the necessary materials, packaged into suitable containers. Such kits may include all the reagents required to detect P. aeruginosa in a sample by means of the methods described herein, and optionally suitable supports useful in performing the methods of the invention.

In one embodiment of the invention the kit contains a nucleotide probe which hybridizes with a nucleic acid molecule of the invention, reagents required for hybridization of the nucleotide probe with the nucleic acid molecule, and directions for its use. In another embodiment of the invention the kit includes antibodies of the invention and reagents required for binding of the antibody to a protein specific for P.aeruginosa in a sample. In still another embodiment of the invention, the kit includes primers which are capable of amplifying a nucleic acid molecule of the invention or a predetermined oligonucleotide fragment thereof, all the reagents required to produce the amplified nucleic acid molecule or predetermined fragment thereof in the polymerase chain reaction, and means for assaying the amplified sequences.

The methods and kits of the present invention have many practical applications. For example, the methods and kits of the present invention may be used to detect P. aeruginosa in any medical or veterinary sample suspected of containing P.aeruginosa. Samples which may be tested include bodily materials such as blood, urine, tissues and the like. Typically the sample is a clinical specimen from wound, burn and urinary tract infections. In addition to human samples, samples may be taken from mammals such as non-human primates, etc. Further, water and food samples and other environmental samples and industrial wastes may be tested.

Before testing a sample in accordance with the methods described herein, the sample may be concentrated using techniques known in the art, such as centrifugation and filtration. For the hybridization and/or PCR-based methods described herein, nucleic acids may be extracted from cell extracts of the test sample using techniques known in the art.

B. Screening Methods

The present inventors have found the Waa (or Rfa) proteins (ie. the proteins encoded by the waa gene cluster, waaF, waaC, waaG and waaP) are involved in the synthesis and assembly of core lipopolysaccharide of P. aeruginosa. Therefore, the invention also contemplates a method for identifying substances that modulate core lipopolysaccharide synthesis or assembly. The substances identified may be agonists or antagonists (i.e. stimulators or inhibitors) of the waa genes or proteins.

(a) Substances that Modulate Protein Activity

The invention contemplates a method of evaluating whether a substance modulates the activity of the Waa proteins of the invention and thereby modulates (ex. enhances or inhibits) core lipopolysaccharide synthesis or assembly. Suitable assays may be designed to identify substances capable of binding the Waa proteins of the invention. A general method of evaluation is to prepare a reaction mixture containing Waa proteins in the presence of a test substance under conditions and for a period of time sufficient for the two components to interact and bind to form a complex which can be removed and/or detected. Control reaction mixtures without the test compound or with a placebo may also be prepared. The formation of complexes or synthesis or assembly of core lipopolysaccharide is detected and the formation of complexes or synthesis or assembly of core lipopolysaccharide in the control reaction but not in the reaction mixture indicates that the test substance modulates the synthesis and assembly of core lipopolysaccharide. The formation of complexes between a Waa protein of the invention and a test substance may be detected using methods known in the art. Generally, at least one of the components is immobilized on a solid substrate which allows the easy separation of unbound components. The solid substrate may be chosen from a number of substrates including microtiter plates, microbeads, dip sticks and resin particles. In order to detect the complexes, generally one of the components is labelled. The label may provide for direct detection such as radioactivity, luminesce or indirect detection such as a labelled antibody or enzyme. Protein-protein interactions may be identified using conventional methods such as co- immunoprecipitation, crosslinking and co-purification through gradients or chromatographic columns.

The test substances used in the above assays may be isolated from a wide variety of sources including libraries of natural or synthetic compounds. Suitable libraries may be commercially available or readily produced. As an example, combinatorial libraries may be screened for substances which can bind to the proteins of the invention. Preferably, the isolated substances will bind tightly to the active sites of the proteins.

Automated high throughput drug screening methods may also be used. Test assays known in the art may be used whereby a large number of compounds may be tested in regard to their biological efficacy. Many computer aided methods have been developed for the generation of substances with a prescribed set of physical, chemical or bioactive properties (see U.S. Pat. No. 5,463,564). Such techniques may be used to isolate substances capable of binding to the Waa proteins of the invention. In one embodiment, automated test systems utilizing computer-controlled robotic systems which allow for the evaluation of the biological effect of up to 1 million substances per robot per year may be used (Kuhlmann J, *Int J Clin Pharmacol Ther,* 35(12):541–552, 1997).

The substances that may be identified using the method of the invention include peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies (e.g. polyclonal, monoclonal, humanized, anti-idiotypic, chimeric, single chain antibodies, fragments, (e.g. Fab, F(ab)$_2$, and Fab expression library fragments, and epitope-binding fragments thereof), and small organic or inorganic molecules. The substance may be an endogenous physiological compound or it may be a natural or synthetic compound. The substances identified using the above methods may be used to develop novel drugs for the treatment of bacterial infections. Novel substances identified using the methods described herein are also within the scope of the invention.

In an embodiment of the invention, where the protein is a transferase enzyme (e.g. WaaG), a method is provided for assaying for a substance that affects core lipopolysaccharide synthesis and assembly in *P. aeruginosa* comprising incubating the protein with a donor and an acceptor, and a test substance which is suspected of affecting the activity of the protein, and determining the effect of the substance by comparing the amount of donor transferred to the acceptor with the amount obtained with a control in the absence of the substance.

In another embodiment of the invention, the protein is an enzyme e.g. an enzyme that phosphorylates heptose residues (WaaP), and a method is provided for assaying for a substance that affects core lipopolysaccharide synthesis and assembly in *P. aeruginosa* comprising incubating a protein of the invention with a substrate of the protein, and a test substance which is suspected of affecting the activity of the protein, and determining the effect of the substance by comparing to a control (e.g. determining if a heptose residue is phosphorylated).

(b) Substances that Modulate waa Gene Expression

The invention contemplates a method of evaluating whether a substance modulates transcription or translation of a waa gene of *P. aeruginosa* and thereby modulates core lipopolysaccharide synthesis or assembly. The method comprises transfecting a cell with an expression vector comprising a waa nucleic acid sequence (ie. waaF, waaC, waaG or waaP) and the necessary elements for the transcription or translation of the nucleic acid; administering a test substance; and comparing the level of expression of the core lipopolysaccharide with the level obtained with a control in the absence of the test substance.

An expression vector comprising a nucleic acid sequence encoding a Waa protein may be constructed having regard to the sequence of the gene using procedures known in the art, or those described above. Suitable transcription and translation elements may be derived from a variety of sources, including bacterial, fungal, viral, mammalian, or insect genes. Selection of appropriate elements is dependent on the host cell chosen, and may be readily accomplished by one of ordinary skill in the art.

The test substances may be isolated from a variety of sources including nucleic acid libraries such as cDNA libraries. Automated systems known in the art (and referred to above) may also be used to isolate novel test substances.

C. Therapeutic Applications

The substances identified by the methods described herein, antisense nucleic acid molecules, and antibodies, may be used for modulating one or both of core lipopolysaccharide synthesis and assembly in *P. aeruginosa.,* and accordingly they may be used in the treatment of bacterial infections. Lipopolysaccharide is a virulence factor of *P. aeruginosa* and substances which can target core lipopolysaccharide biosynthesis in *P. aeruginosa* to change the organism so that it is devoid of, or has reduced lipopolysaccharide, will be useful in rendering the bacterium susceptible to attack by host defense mechanisms. The substances identified by the methods described herein, antisense nucleic acid molecules, and antibodies are preferably used to treat infections caused by *P. aeruginosa*. The agents that inhibit waa proteins may be used to treat infections caused by *P. aeruginosa* serotype 03 which is a predominant clinical isolate. It will be appreciated that the substances may also be useful to treat infections caused by other members of the family Pseudomonadaceae (eg. *Burkholderia cepacia* and *P. pseudomallei*), and to treat other bacteria which produce O-antigen, (e.g. other gram negative bacteria such as *E. coli, S. enterica, S. typhimurium, Vibrio cholera, H.influenze, Yersinia entercolitica, Shigella dysenteriae,* and *Shigella flexneri*).

(i) Inhibitors of Protein Activity

Core lipopolysaccharide synthesis and assembly may be inhibited by administering an agent that inhibits one or more Waa proteins of the invention. Accordingly, the present invention provides a method of treating or preventing a bacterial infection comprising administering an effective amount of an agent that inhibits a Waa protein to an animal in need thereof.

The term "effective amount" as used herein means an amount effective and at dosages and for periods of time sufficient to produce the desired effect.

The term "animal" as used herein means all members of the animal kingdom including mammals, preferably humans.

In one embodiment, an agent that inhibits a Waa protein of the invention is an antibody to a Waa protein. Antibodies to Waa proteins of the invention may be prepared according to the methods described herein above.

In another embodiment, an agent that inhibits a Waa protein of the invention may be a Waa binding substance as identified using the screening methods identified hereinabove.

In a preferred embodiment, the bacterial infection is an infection caused by Pseudomonas aeruginosa.

(ii) Inhibitors of Gene Activity

Core lipopolysaccharide synthesis and assembly may be inhibited by administering an agent that interferes with the expression of one or more waa genes of the invention. Accordingly, the present invention provides a method of treating or preventing a bacterial infection comprising administering an effective amount of an agent that inhibits a waa gene to an animal in need thereof.

In one embodiment, the agent is an antisense oligonucleotide prepared according to the methods described hereinabove. In another embodiment, the agent is a substance that binds a waa gene identified according to the screening methods defined hereinabove.

(iii) Pharmaceutical Compositions

The substances identified using the methods described herein may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, adds and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Antisense oligonucleotides of the invention may be delivered using viral or non-viral vectors. Sequences may be incorporated into cassettes or constructs such that an antisense oligonucleotide or ribozyme of the invention is expressed in a cell. Generally the construct contains the proper transcriptional control region to allow the oligonucleotide or antisense oligonucleotide to be transcribed in the cell.

Vectors are known or can be constructed by those skilled in the art and should contain all expression elements necessary to, achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et al (1986) and include, for example, stable or transient transfection, lipofection, electroporation and infection with recombinant viral vectors.

Introduction of nucleic acids by infection offers several advantages. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

The reagents suitable for applying the methods of the invention to identify substances that affect O-antigen synthesis and assembly in *P. aeruginosa* may be packaged into convenient kits providing the necessary materials packaged into suitable containers. The kits may also include suitable supports useful in performing the methods of the invention.

The utility of the substances, antibodies, and compositions of the invention may be confirmed in experimental model systems.

(iv) Vaccines

The present invention also includes a vaccine against a bacterial infection, preferably Pseudomonas aeruginosa, comprising an effective amount of one or more Waa proteins of the invention in admixture with a suitable diluent or carrier.

In one embodiment, the vaccine comprises an effective amount of a WaaP protein in admixture with a suitable diluent or carrier. In another embodiment, the vaccine comprises an effective amount of a WaaF protein in admixture with a suitable diluent or carrier. In a further embodiment, the vaccine comprises an effective amount of a WaaC protein in admixture with a suitable diluent or carrier. In yet another embodiment, the vaccine comprises an effective amount of a WaaG protein in admixture with a suitable diluent or carrier.

The vaccines of the invention can be intended for administration to all animals including mammals, avian species and fish, preferably humans and various other mammals including bovines, equines and swine.

The vaccines of the invention may be administered in a convenient manner such as intravenously, intramuscularly, subcutaneously, intraperitoneally, intranasally or orally. The dosage will depend on the nature of the infection, on the desired effect, on the chosen route of administration and other factors known to persons skilled in the art.

A vaccine of the invention may be a nucleic acid vaccine containing a nucleic acid molecule encoding a Waa protein of the invention. In such an embodiment, the Waa protein is produced in vivo in the host animal. The vaccines containing nucleic acids may be delivered using suitable vectors including retroviral vectors, adenoviral vectors and DNA virus vectors.

A vaccine of the present invention may be tested in animal systems in vivo to confirm their efficacy in the prophylaxis or treatment of infectious diseases caused by Pseudomonas aeruginosa and to determine appropriate dosages and routes of. administration.

The antibodies to the Waa proteins of the invention (as prepared hereinabove) may also be used as a means of passive immunization.

The invention will be more fully understood by reference to the following examples. However, the examples are merely intended to illustrate embodiments of the invention and are not to be construed to limit the scope of the invention.

EXAMPLE 1

To gain a thorough understanding of the functional role of LPS in host-bacteria interactions, an investigation of the genetics and synthesis of the core of P. aeruginosa is necessary. Two genes whose deduced amino acid sequence show homology to WaaP and WaaG of Salmonella typhimurium and E. coli have been cloned from P. aeruginosa O5. The WaaP protein may phosphorylate an inner-core heptose residue. waaP and waaG were subcloned from a 6.1 fragment of chromosomal DNA. The nucleic acid sequences for the waaP and waaG genes are shown in FIG. 3 and FIG. 8, respectively, and their deduced amino acid sequences are shown in FIG. 4 and FIG. 9, respectively. The four waa genes of P. aeruginosa are arranged contiguously in an operon with the following gene order waaF, waaC, waaG and waaP. In the enterobacteriaceae the genes for heptosyl transferases are located on a separate operon from the hexosyl transferases. The function of the proteins will be tested by complimentation of specific S. typhimurium mutants, and knockout mutations of the genes in P. aeruginosa.

EXAMPLE 2

Materials and Methods
Bacterial Strains and Culture Conditions

The bacterial strains used in this study are listed in Table 1. Miller's Luria broth (Difco Laboratories, Detroit, Mich.) was used for maintenance of bacterial strains. Pseudomonas Isolation Agar (PIA; Difco) and Davis minimal media (Difco) were used for selection of transconjugants following mating experiments. Antibiotics used in selection media included ampicillin at 100 µg/ml for E. coli and carbenicillin at 450 µg/ml for P. aeruginosa; tetracycline at 15 µg/ml for E. coli and 90 µg/ml for P. aeruginosa (250 µg/ml in PIA); gentamicin at 10 µg/ml for E. coli and 300 µg/ml for P. aeruginosa. Bacteriophage-sensitivity tests were done following the method of WiLkinson et al. (J. Gen. Microbiol. 70:527–554, 1972).

DNA Procedures

Plasmid DNA was isolated in small-scale amounts by utilizing the alkaline lysis method of Bimboim and Doly (Nucleic Acids Res. 7:1513–1523, 1979) while large-scale preparations were obtained using the Qiagen midi plasmid kit (Qiagen Inc., Chatsworth, Calif.) following manufacturer's instructions. P. aeruginosa whole genomic DNA was isolated according to the method of Goldberg and Ohman (J. Bacteriol. 158:1115–1121, 1984) Restriction enzymes were purchased from GIBCO/BRL and Boehringer-Mannheim (Mannheim, Germany). T4 DNA ligase, T4 DNA polymerase and alkaline phosphatase were purchased from Boehringer-Mannheim. All enzymes were used following suppliers' recommendations. DNA was transformed into E. coli and S. enterica serovar Typhimurium by electroporation using a Bio-Rad Gene Pulser electroporation unit (Bio-Rad Laboratories, Richmond, Calif.) and by following protocols supplied by the manufacturer. Electrocompetent cells of E. coli and S. enterica serovar Typhimurium were prepared according to the method of Binotto et al. (J. Microbiol. 37:474–477, 1991). Recombinant plasmids were mobilized from E. coli SM10 to P. aeruginosa using the method of Simon et al. (Bio/Technology 1:784–791, 1983). Genomic DNA was transferred to a Zetaprobe membrane (Bio-Rad) by capillary transfer following the manufacturer's instructions. Southern hybridizations were done as described previously (de Kievit, T. R. et al., Mol. Microbiol. 16:565–574, 1995).

Construction of a P. aeruginosa Gene Library

A genomic library of P. aeruginosa strain PAO1 was constructed according to the method of Goldberg and Ohman (J. Bacteriol. 158:1115–1121, 1984) with the following modifications. Partial Sau3AI fragments of predominantly 2 to 10 kb were ligated with BamHI-digested vector pBluescript. The recombinant plasmids were electrotransformed into E. coli strain DH5a. Transformants were allowed to recover in SOC media for several hours before being subjected to large-scale plasmid extraction. The plasmid library was then electrotransformed into waaC and waaF mutants of S. enterica serovar Typhimurium.

DNA Sequencing

DNA sequence analysis of the O5 waaF and waaC genes was performed by the MOBIX facility (McMaster University, Hamilton ON). Sequencing of the 1.5-kb insert of pCOREf1 and the 2.2-kb insert of pCOREc2 was done using a model 373A DNA sequencing unit (Applied Biosystems, Foster City, Calif.). An Applied Biosystems model 391 DNA synthesizer was used to generate oligodeoxynucleotide sequencing primers. The Taq DyeDeoxy™ Terminator Cycle Sequencing Kit (Applied Biosystems) was used for cycle sequencing reactions which were carried out in an Ericomp (San Diego, Calif.) model TCX15 thermal cycler.

Sequence Analysis

The computer software program Gene Runner for Windows (Hastings Software, New York, N.Y.) was used for nucleic acid and amino acid sequence analysis. Homology searches of the nucleotide and amino acid sequences of the P. aeruginosa waaC and waaF genes were performed using EMBL/GenBank/PDB and SWISS-PROT (release 28.0) databases (Altschul, S. F. et al. J. Mol. Biol. 215:403–410, 1990; Gish, W. and D. J. States, Nature Genet. 3:266–272, 1993).

Maxicell Analysis of Plasmid DNA

Analysis of plasmid-encoded proteins was done according to the method of Sancar et al. (J. Bacteriol. 137:692–693, 1979). Maxicells were prepared as described previously by Lightfoot and Lam (Mol. Microbiol. 8:771–782, 1993), with the following modifications. Plasmids were electroporated into E. coli strain CSR603. Overnight cultures were diluted 1:50 in 10 ml of supplemented Davis media lacking antibiotics. The cultures were grown to mid-logarithmic phase, after which time they were irradiated for 30 s at 500 $\mu$W/cm$^2$ with a germicidal lamp. Expressed proteins were labelled using a Trans$^{35}$S-labeled methionine (ICN Biomedicals).

Pulsed-field Gel Electrophoresis

Procedures for PFGE were as described by Lightfoot and Lam (Mol. Microbiol. 8:771–782, 1993).

Mutagenesis of the waaC and waaF Genes of P. aeruginosa

Using a previously described gene-replacement strategy (de Kievil, T. R. et al., Mol. Microbiol. 16:565–574, 1995), we attempted to generate waaC and waaF null mutants of P. aeruginosa. The suicide vector that was used in these experiments, pEX100T, contains a copy of the Bacillus subtilis sacB gene which imparts sucrose sensitivity to Gram-negative organisms (Schwelzer, H. P. and T. T. Huang, Gene 158:15–22, 1995). The presence of the vector-associated sacB gene in the chromosome of the merodiploids renders them sucrose-sensitive. Therefore, streaking cells on sucrose-containing medium allows separation of true recombinants from the more frequently occurring merodiploids.

Preparation of LPS

LPS used in sodium dodecyl sulfate-polyacrylamide gel electrophoresis (SDS-PAGE) and Western immunoblotting experiments was prepared according to the proteinase K digest method of Hitchcock and Brown (J. Bacteriol. 154:269–277, 1983).

SDS-PAGE

The discontinuous SDS-PAGE procedure of Hancock and Carey (J. Bacteriol. 140:902–910, 1979) utilizing 15% running gels was used. LPS separated by SDS-PAGE was visualized by silver-staining according to the method of Dubray and Bezard (Anal. Biochem. 119:325–329, 1982).

Immunoblotting

The Western immunoblotting procedure of Burnette (Burnette, W. N., Anal. Biochem. 112:195–203, 1981) was used with the following modifications. Nitrocellulose blots were blocked with 3% (w/v) skim milk followed by incubation with polyclonal antisera raised against wild-type S. enterica serovar Typhimurium strain SL3770. The blots were developed at room temperature, using goat anti-rabbit F(ab')$_2$ alkaline phosphatase-conjugated antibody (Jackson Immunoresearch Laboratories, West Grove, Pa.) and a substrate consisting of 30 mg of Nitro Blue Tetrazolium and 15 mg of 5-bromo-4-chloro-3-indolyl phosphate toluidine (Sigma, St. Louis, Mo.) in 100 ml of 0.1 M bicarbonate buffer (pH 9.8).

Immunogen Preparation and Polyclonal Antibody Production

For immunizing rabbits, formalin-fixed whole cells of S. enterica serovar Typhimurium wild-type strain SL3770 were used. Immunogen was prepared according to Lam et al. (Infect. Immun. 42:88–98, 1983). Two New Zealand white female rabbits were used for production of polyclonal sera. Preimmune serum was collected and pooled to check for preimmune nonspecific antibodies. Immunization and bleeding of the animals were performed according to Lam et al. (Infect. Immun. 42:88–98, 1983). All sera were collected and stored at −20° C. until used. To determine the optimal dilution of the polyclonal sera, Western blots of LPS from strain SL3770 were incubated with sera which had been serially diluted ten-fold in phosphate-buffered saline (PBS). A 1 to 10,000 dilution was used in subsequent Western immunoblotting experiments.

Nudeotide Sequence Accession Numbers

The nucleotide sequences of the P. aeruginosa waaC and waaF genes were submitted to GenBank and the accession numbers are as follows: U70982 (waaC) and U70983 (waaF).

Results

Isolation of the waaC and waaF Genes of P. aeruginosa

Figure 11:
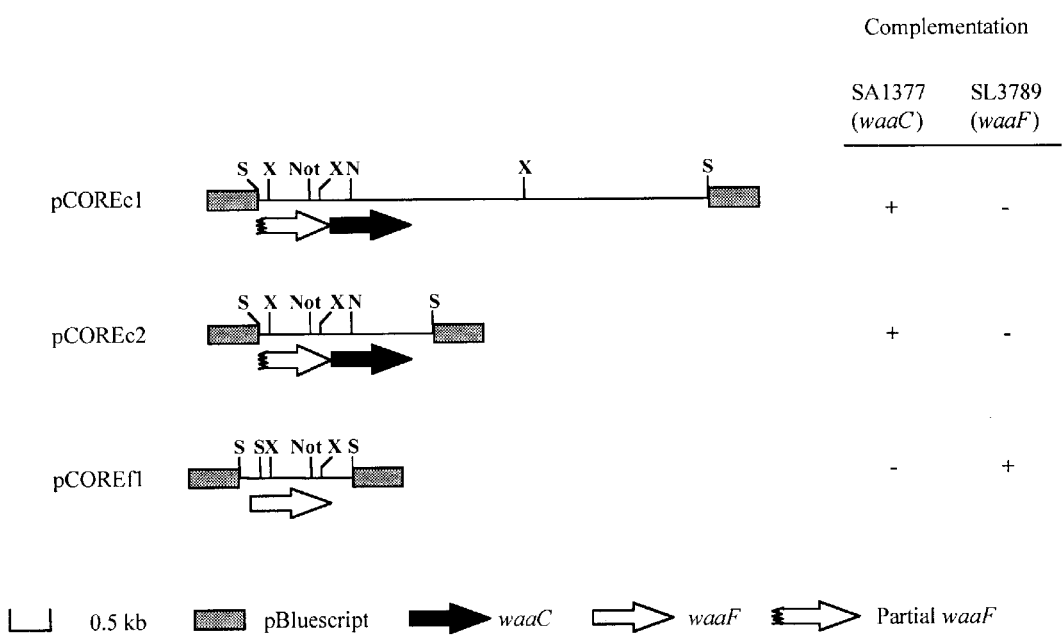
FIG. 11 are restriction maps of the chromosomal inserts of pCOREc1, pCOREc2, and pCORE f1.

A P. aeruginosa serotype O5 plasmid library was generated in vector pBluescript, and electrotransformed into S. enterica serovar Typhimurium SA1377 (waaC–mutant) and SL3789 (waaF–mutant). After recovery in SOC media, Salmonella cells were plated on L agar containing novobiocin (Nb; 100 $\mu$g/ml) and ampicilin (Amp; 100 $\mu$g/ml) and incubated at 37° C. overnight. Nb was added to the medium because S. enterica serovar Typhimurium deep-rough strains are sensitive to this antibiotic. Therefore, cells able to grow on this medium are those that do not have the deep-rough phenotype. Several SA1377 and SL3789 Nb$^r$, Amp$^r$ transformants were isolated. Plasmids were extracted from these transformants and retransformed into the appropriate Salmonella mutants to ensure their ability to confer the Nb$^r$ phenotype. Two plasmids which were able to complement the Salmonella waaC mutant, SA1377, were identified. Restriction enzyme analysis of the two plasmids revealed that they contained 6.1-kb and 2.2-kb inserts, and the plasmids were designated pCOREc1 and pCOREc2, respectively. Similarly, a plasmid containing a 1.5-kb insert, designated pCOREf1, was able to restore growth on Nb in the Salmonella waaF mutant. Transformation of pCOREc1 and pCOREc2 into the waaF mutant did not result in restoration of smooth LPS production, indicating that a complete waaF gene was not present on either of these plasmids. The restriction maps of pCOREc1, pCOREc2 and pCOREf1 are shown in FIG. 11.

Characterization of LPS Expressed by Salmonella SA1377 (pCOREc1), SA1377(pCOREc2), and SL3789 (pCOREf1) Transformants LPS expressed by the SA1377 and SL3789 transformants, containing the putative P. aeruginosa waaC and waaF genes, was characterized by phage sensitivity, SDS-PAGE analysis, and Western immunoblot analysis. The phage FFM, which is specific for deep-rough Salmonella LPS (WiLison et al, J. Gen. Microbiol. 70:527–554, 1972), was added to the freshly inoculated Salmonella transformants and the wild type S. enterica strain SL3770. The phage readily lysed the two core mutants, but it had no effect on either the wild-type strain SL3770, or the Salmonella transformants containing the P. aeruginosa waaC and waaF genes. Analysis of LPS by SDS-PAGE revealed that transformant strains SL3789 (pCOREf1) and SA1377(pCOREc2), as well as SA1377

(pCOREc1), all expressed long-chain LPS. In Western immunoblots, antiserum raised against wild-type *S. enterica* serovar Typhimurium strain SL3770 reacted with high molecular weight LPS from both SL3770 and the transformants. These results confirmed the ability of the *P. aeruginosa* waa genes to restore smooth LPS expression in the mutants. A weak reaction of high molecular weight LPS bands from the Salmonella waaC and waaF mutants, strains SA1377 and SL3789 respectively, with the *S. enterica* strain SL3770-specific antiserum was also observed. The presence of long-chain O antigen indicates that these mutants are either leaky or possibly that "O hapten", which is not capable of attaching to a heptoseless core on the core-lipid A of these mutants, is present in the samples.

Nucleotide Sequence Determination of waaC and waaF

The 2.2-kb insert of pCOREc2, containing the waaC gene, and the 1.5-kb insert of pCOREf1, containing the waaF gene, were subjected to double-strand nucleotide sequencing. Analysis of the DNA sequence encoded by pCOREc2 revealed one open reading frame (ORF) coding for a protein of 355 amino acids with a predicted mass of 39.8 kDa. Sequence analysis of pCOREf1, showed one ORF which could encode a protein of 345 amino acids with a deduced size of 38.4 kDa.

Comparison of the deduced amino acid sequences of the *P. aeruginosa* WaaC and WaaF proteins with those of other reported proteins in the GenBank and SWISS-PROT data bases (Gisg, W. and D. J. States Nature Genet. 3:266–272, 1993, Altschul, S. E., et al., J. Mol. Biol. 2125:403–410, 1990), revealed that the WaaC protein of *P. aeruginosa* is 52.7% identical to the WaaC protein of *S. enterica* serovar Typhimurium, and 52.4% identical to that of *E. coli*. Similarly, the *P. aeruginosa* WaaF protein showed 49.0% and 49.3% identity with the WaaF proteins of *S. enterica* serovar Typhimurium and *E. coli*, respectively.

Maxicell in vivo Protein Expression

Maxicell analysis was performed to confirm that the ORFs contained on the DNA inserts of pCOREc2 and pCOREf1 encoded proteins consistent with the predicted sizes. *E. coli* strain CSR603, containing pBluescript alone, was used as the vector control. A 31-kDa protein and a 28.5-kDa protein, corresponding to β-lactamase, were found in all of the samples. When pCOREf1 was used in protein expression experiments, a 39 kDa protein was observed, corresponding well with 38.4 kDa deduced from the nucleotide sequence. In cells expressing pCOREc2, a 40-kDa protein was found which is consistent with 39.8-kDa predicted from the sequence data. In addition, a 47-kDa protein was observed; however, no ORF corresponding to a protein of this size was identified. Plasmid pCOREc2 contains the entire waaC gene plus 176 bp of a downstream gene which is predicted to encode a truncated protein of approximately 7 kDa. Two possibilities exist to account for the presence of this 47-kDa protein. First, the protein may result because the incomplete ORF downstream of waaC is being translated into vector sequences. Examination of the downstream region including the pBluescript sequence, however, suggests that this is not the case. Second, a fusion protein could be produced by continued translation of waaC into the downstream sequence.

Chromosomal Mapping of Cloned waa Genes

PFGE was used to separate SpeI- and DpnI-digested PAO1 chromosomal DNA for mapping of the *P. aeruginosa* waa genes. The inner core biosynthetic genes were located on the PAO1 chromosome by Southern hybridization using a digoxigenin-labelled probe generated from the 2.2 kb insert of pCOREc2. This DNA insert contains all of the waaC gene and most of waaF. In Southern blots, the waa-specific probe hybridized to a SpeI-fragment of approximately 450 kb which corresponds to restriction fragment SpB. SpB spans 0.9 to 6.6 min on the 75-min map (Farinha M. A. et al., Infect. Immun. 61:1571–1573, 1993). In blots of DpnI-digested chromosomal DNA, the probe hybridized to a 269 kb fragment, DpJ, which is actually a doublet composed of two 269-kb fragments. The two fragments span 75.0 to 3.3 min (DpJ1) and 3.3 to 6.7 min (DpJ2) on the map (Farinha M. A. et al., Infect. Immun. 61:1571–1573, 1993). Therefore, genes involved in biosynthesis of the LPS inner core region lie between 0.9 and 6.6 min.

Southern hybridization of the Twenty *P. aeruginosa* Serotypes Using a Waa-specific Probe To determine whether the waaC and waaF genes were present in all twenty serotypes, Southern hybridization analysis was performed. The waa probe used to analyze PFGE blots was employed to probe BamHI-, EcoRI-, and KpnI-digested chromosomal DNA. The probe hybridized to a common 7.5-kb BamHI fragment in all twenty serotypes except O12, where the probe hybridized to a 12.0-kb fragment. Similarly, the waa-specific probe hybridized to a 4.2-kb EcoRI fragment in all serotypes except O12, where the probe hybridized to a 5.0-kb band, and serotype O4, in which case the probe hybridized to an additional 9.5-kb band. In Southern blots of KpnI-digested chromosomal DNA, the probe hybridized to various-sized fragments from the twenty serotypes. Therefore, the two waa genes appear to be present in all twenty *P. aeruginosa* serotypes, although the sizes of the restriction enzyme fragments are not strictly conserved.

Generation of *P. aeruginosa* Chromosomal waaC and waaF Mutants

Using a gene replacement strategy, attempts were made to generate waaC and waaF mutants of *P. aeruginosa*. The first approach involved cloning the 2.2-kb insert of pCOREc2 into gene-replacement vector pEX100T (Schwelzer, H. P. and T. T. Hoang Gene 158:15–22, 1995). An 875-bp $Gm^r$ cassette was cloned into a unique NruI site within the waaC coding region and the resulting plasmid was designated pCOREk1. pCOREk1 was mated independently into two strains of *P. aeruginosa*, namely PAO1 and PAK. During selection of transconjugants, various growth conditions were used to overcome possible deleterious effects associated with the deep-rough mutations. Conditions included growing cells at 30° C. as well as 37° C., plating cells on minimal media containing gentamicin, in addition to PIA-gentamicin, to select for *P. aeruginosa* harboring the $Gm^r$ cassette; and finally, plating cells on media supplemented with 20% sucrose to increase the osmotic strength of the medium for stabilization of outer membranes. Despite the fact that numerous merodiploids were isolated, no true waaC recombinants were identified. The next approach involved cloning the larger 6.1-kb insert of pCOREcl into pEX100T. A larger piece of DNA was used to increase the likelihood of a double cross-over event. This time, the $Gm^r$ cassette was cloned in both orientations into a NotI site within the waaF coding region. The $Gm^r$ cassette contains a promoter, but no transcriptional terminator (Schwelzer, H. P. BioTechniques 15:831–833, 1993). If genes downstream of waaF are transcribed from an upstream promoter, cloning the cassette promoter in the direction opposite to that of transcription (plasmid pCOREk2) should affect expression of downstream genes, as well as waaF. Conversely, if the cassette is cloned in the other orientation (plasmid pCOREk3), transcription of downstream genes should occur. Plasmids pCOREk2 and pCOREk3 were mated into *P. aeruginosa* and transconjugants were grown under the conditions described above. Again, no true recombinants were obtained. Insertion of the cassette within the chromosome of the merodiploids was verified using Southern blot analysis and a probe specific for the Gm$^r$ cassette. In all cases, the insertion occurred downstream of waaC.

Discussion

Because the *P. aeruginosa* waaC and waaF genes readily complement corresponding *S. enterica* serovar Typhimurium mutants, sufficient similarity must exist between the proteins of these two organisms to allow them to be functionally exchangeable. Inspection of the protein alignments reveals that there is a region near the beginning of the WaaC sequence, corresponding to the N-terminus of the protein, of markedly high similarity. Fifty-four of the first 64 amino acids (84%) in the *P. aeruginosa* WaaC protein are identical to those found in *E. coli* and *S. enterica* serovar Typhimurium. Other regions throughout the WaaC protein are highly homologous; however, none are as significant as the N-terminus. In contrast, regions of homology between the *P. aeruginosa* WaaF protein and those of *S. enterica* serovar Typhimurium and *E. coli* are more evenly distributed throughout the sequence. These conserved regions likely represent functionally important domains in the two heptosyltransferase proteins. Interestingly, the WaaC protein of Neisseria gonorrhoeae shows even less identity (36%) with that of *S. enterica* serovar Typhimurium and yet the gene specifying this protein is able to complement a Salmonella waaC mutant (Zhou, D. et al. Mol. Microbiol. 14:609–618, 1994).

In *S. enterica* serovar Typhimurium, the waaF and waaC genes are contiguous and cotranscribed from an upstream promoter (Sirisena, D.M. et al., J. Bacteriol. 176:2379–2385, 1994). gmhD (formerly rfaD) lies upstream of waaF, and waaL (formerly rfaL) is located downstream of waaC. These four genes together comprise one of the three Salmonella waa operons. A similar contiguous arrangement of the waaF and waaC genes was observed in *P. aeruginosa*. waaF lies upstream of waaC, and the two genes have overlapping termination and initiation codons. In P. aeruginosa, there appears to be a gene directly upstream of waaF; the stop codon of which overlaps the waaF start sequence. Only 176 bp have been sequenced downstream of the *P. aeruginosa* waaC gene, however, this region has amino acid homology with the waaG (formerly rfaG) gene product of *E. coli* (74% over 174 of the 176 bp) (Clemeniz, T., J. Bacteriol. 174:7750–7756, 1992, Parker, C. T. et al., J. Bacteriol. 174:930–934, 1992). waaG encodes a glucosyltransferase which adds the first hexose, a glucose residue, onto the inner core. In Salmonella and *E. coli* K12, waaG is located at the distal end of another waa operon (Schnaitman, C. A., et al., J. Bacteriol. 173:7410–7411, 1991). Although the inner core of *P. aeruginosa* is quite similar to that of *S. enterica* and *E. coli*, the outer core region differs substantially. The first hexose sugar found in the outer core of both *S. enterica* serovar Typhimurium and *E. coli* is Glc; whereas in *P. aeruginosa*, it is a GalN residue. Another unique feature of the *P. aeruginosa* outer core is the presence of the amino acid L-alanine. In light of these and other structural differences, it is not surprising that the genetic arrangement of the waa locus may differ in *P. aeruginosa*, particularly with respect to genes involved in synthesis of the outer core region.

EXAMPLE 3

Functional Analysis of waaP and its Encoded Protein, WaaP

Figure 12:
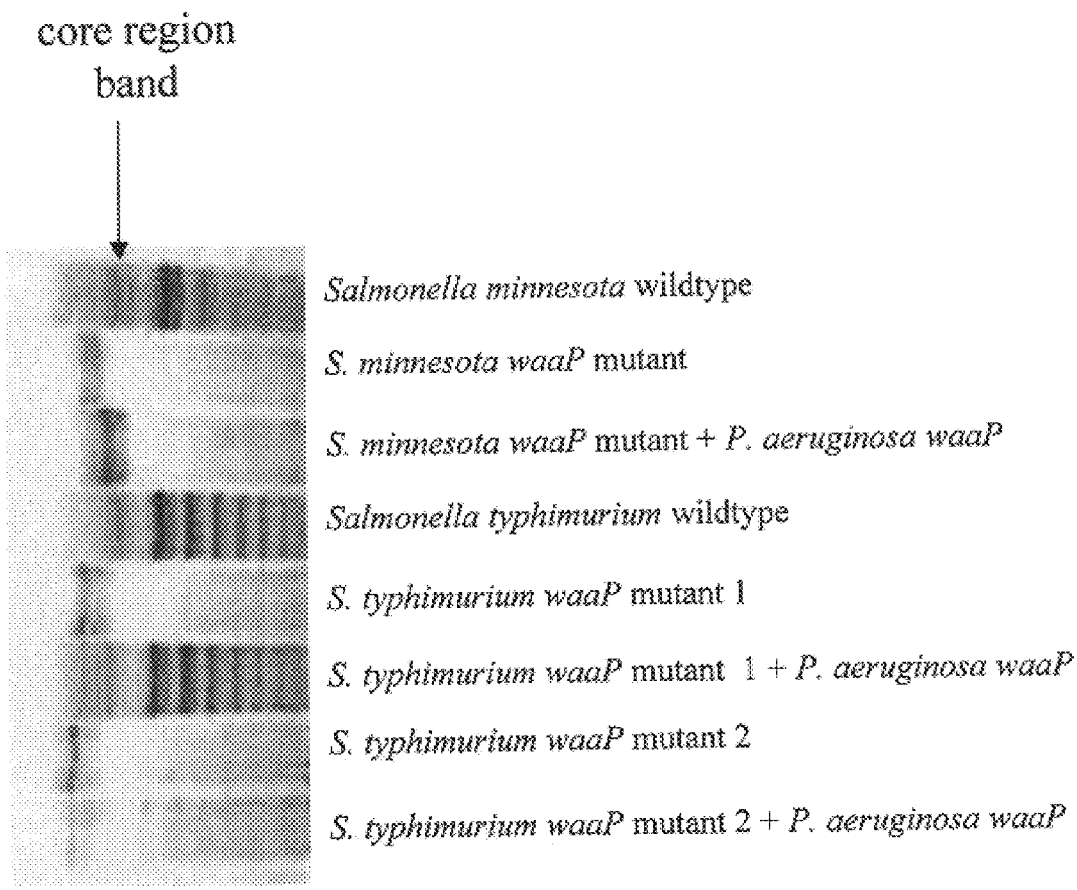
FIG. 12 is a gel showing the core region lipopolysaccharide of various strains of bacteria.

1) WaaP$_{PAO1}$ could complement Salmonella waaP-mutants and Restored Full Ladder Banding Pattern Virtually Identical to Wildtype Strain By Tricine gel analysis (method according to de Kievit, T. R. and J. S. Lam. 1994. Monoclonal antibodies that distinguish inner core, outer core, and lipid A regions of *Pseudomonas aeruginosa* lipopolysaccharide. J. Bacteriol. 176:7129–7139) of the core region of the lipopolysaccharides of the strains listed in Table 2 we have shown that the waaP gene of *Pseudomonas aeruginosa* is functionally homologous to that of *Salmonella enterica* serovar Typhimurium and *Salmonella minnesota* (see FIG. 12). Separation of core-region-bands on the gel shows that there is an increase in the molecular weight of Salmonella waaP mutant cores when waaPPAO1 is present in trans. The size of the core is more similar to that of the wildtype strain, indicating that there is a higher degree of completion of the core with waaPPAO1 present. Furthermore, complimentation of SH7770 by waaPPAO1 increased the amount of fully completed cores with attached O antigen, giving a ladder pattern virtually identical to that of wildtype strain SL696.

2) Possible Mechanism of Complimentation of waaP-minus Mutants with waaP$_{PAO1}$ Helander, I. M. et al., (1989. rfap (waaP) mutants of *Salmonella typhimurium*. Eur. J. Biochem. 185:541–546) analyzed SH7770 by Urea/SDS/PAGE analysis and determined that the predominant core type being produced was of the truncated, RC chemotype. This RC chemotype is a result of a mutation that prevents the addition of galactose and more distal sugars to the outer core. However, they found that there were some complete cores being produced. This suggests that the absence of phosphate groups transferred to the inner core region by waaP reduces the efficiency of sugar transfer to the more distal regions of the Salmonella core. Muhlradt et al. (1968. Biochemical studies on lipopolysaccharides of Salmonella R mutants: Evidence for a phosphorylating enzyme in lipopolysaccharide biosynthesis. Eur. J. Biochem. 4:139–145) showed that treating the core of a *S. minnesota* waaP mutant with enzyme extract of a waaP+ strain increased the efficiency of transfer of galactose to the outer core. Our results suggest that waaP$_{PAO1}$ increases the amount of complete core being produced by Salmonella waaP–strains, presumably due to the addition of phosphate to the inner core allowing more efficient transfer of sugars to the outer core.

Having illustrated and described the principles of the invention in a preferred embodiment, it should be appreciated to those skilled in the art that the invention can be modified in arrangement and detail without departure from such principles. All modifications are claimed that come within the scope of the following claims.

All publications, patents and patent applications referred to herein are incorporated by reference in their entirety to the same extent as if each individual publication, patent or patent application was specifically and individually indicated to be incorporated by reference in its entirety.

TABLE 1

Bacterial Strains and Plasmids

| Strains or plasmid | Genotype or relevant characteristics | Reference or source |
|---|---|---|
| Strains | | |
| *P. aeruginosa* | | |
| FAO1 | Serotype 05; A[+] B[+] | 23 |
| PAK Paranchych* | Serotype 05 | W |
| *E. Coli* | | |
| DH5α | supE44 hsdR17 recA1 endA1 gyrA96 thi-I relA1 | GIBCO/BRL |
| SM10 | thi-I thr leu tonA lacY supE recA RP4-2-Tm Mu Km[r] | 46 |
| *S. enterica* serovar Typhimurium | | |
| L3770 | waa[+] | 40 |
| SA1377 | waaC630 | 8 |
| SL3789 | waaF577 | 40 |
| Plasmids | | |
| pBluescript-II Biosciences vector KS | Ap[r] | P D I |
| pEX100T | Gene replacement vector, ori1[+] sacB[+] Ap[r] | 45 |
| pUCPGm | Source of Gm[r] cassette; Ap[r] Gm[r] | 44 |

*W. Paranchych, University of Alberta, Edmonton, Alberta, Canada

TABLE 2

Table of strains used in characterizing the waaP gene of *Pseudomonas aeruginosa* sertoype O5 (PAO1).

| Strain | Relevant genotype | Origin of reference |
|---|---|---|
| *Salmonella enterica* serovar Typhimurium | | |
| SL696 | waa+ | Helander et al. |
| SH7770 | waaP– | Helander et al. |
| SH7770/pAW12 | waaPPAO1 | This work |
| SH8572 | waaP– | Helander et al. |
| SH8572/pAW12 | waaPPAO1 | This work |
| *Salmonella minnesota* | | |
| SH971112 | waa+ | a |
| MR5a | waaP– | b |
| MR5a/pAW12 | waaPPAO1 | This work | a Dr. C. Poppe, Health of Animals Laboratory, Guelph, Ontario, Canada.
b Dr. K. E. Sanderson, Salmonella genetic stock centre, Calgary, Alberta, Canada.

We claimed:

1. A purified and isolated nucleic acid molecule encoding a protein involved in the synthesis and assembly of core lipopolysaccharide in *P. aeruginosa* which comprises (a) a nucleic acid sequence as set forth in SEQ ID NO: 1, wherein T can also be (b) a nucleic acid sequence fully complementary to the sequence as claimed in (a); or (c) a nucleic acid molecule differing from the nucleic acid sequence as claimed in (a) or (b) in codon sequences due to the degeneracy of the genetic code.

2. A recombinant molecule for transformation of a host cell comprising the nucleic acid molecule as claimed in claim 1 and an expression control sequence operatively linked to the nucleic acid molecule.

3. A transformant host cell including the recombinant molecule as claimed in claim 1.

4. A kit for detecting the presence of the nucleic acid molecule as claimed in claim 1 in a sample comprising a nucleotide probe that hybridizes with the nucleic acid molecule under stringent hybridization conditions which use 6.0× sodium chloride/sodium citrate (SSC) at about 45° C., followed by a wash of 2.0×SSC at about 50° C.

* * * * *

SEQUENCE LISTING

```
<160> NUMBER OF SEQ ID NOS: 8

<210> SEQ ID NO 1
<211> LENGTH: 807
<212> TYPE: DNA
<213> ORGANISM: Pseudomonas aeruginosa rfaP (waaP)
<220> FEATURE:
<223> OTHER INFORMATION: Description of Organism: Pseudomonas aeruginosa
      serotype O5 strain PAO1

<400> SEQUENCE: 1
atgaggctgg tgctggaaga gccgttcaag cgcctgtgga acgggcgcga cccgttcgag      60
gcggtggagg cgctgcaagg caaggtctac cgcgaactgg aagggcgccg caccctgcgc     120
accgaggtcg acgggcgtgg ctacttcgtc aagatccacc gtggcatcgg ctggggcgag     180
atcgccaaga acctgctcac cgccaagctc ccggtgctcg gcgcgcgcca ggagtggcag     240
gccatccggc gcctgcacga ggccggcgta gcgaccatga ccgcggtcgc ctacggcgag     300
cgcggcagcg atccggcgcg gcagcattcc ttcatcgtca ccgaggaact ggcgccgacc     360
gtggacctcg aggtgttctc ccaggactgg cgcgaacgtc ctccaccgcc gcggctcaag     420
cgcgcgctgg tcgaggcggt ggcgcggatg gtcggcgaca tgcaccgtgc cggagtcaac     480
catcgcgact gctacatctg tcatttcctg ttgcacaccg acaagccggt gagcgcggac     540
gatttccgcc tctcggtgat cgatctgcac cgtgcccaga cccgcgacgc cacgccgaaa     600
cgctggcgta acaaggatct ggcggcattg tatttctctg cgctggacat cggactgacg     660
```

-continued

```
cgtcgcgaca agctacgctt cctgcgcacc tatttccgcc ggccgttgcg cgagatactg      720
cgcgacgagg ccggcctgct ggcctggatg gaacgccagg cggaaaaact ctacgaacgc      780
aagcagcgtt acggagacct gctctga                                          807
```

<210> SEQ ID NO 2
<211> LENGTH: 268
<212> TYPE: PRT
<213> ORGANISM: Pseudomonas aeruginosa RfaP (WaaP)
<220> FEATURE:
<223> OTHER INFORMATION: Description of Organism: Pseudomonas aeruginosa serotype O5 strain PAO1

<400> SEQUENCE: 2

```
Met Arg Leu Val Leu Glu Glu Pro Phe Lys Arg Leu Trp Asn Gly Arg
  1               5                  10                  15

Asp Pro Phe Glu Ala Val Glu Ala Leu Gln Gly Lys Val Tyr Arg Glu
                 20                  25                  30

Leu Glu Gly Arg Arg Thr Leu Arg Thr Glu Val Asp Gly Arg Gly Tyr
             35                  40                  45

Phe Val Lys Ile His Arg Gly Ile Gly Trp Gly Glu Ile Ala Lys Asn
         50                  55                  60

Leu Leu Thr Ala Lys Leu Pro Val Leu Gly Ala Arg Gln Glu Trp Gln
 65                  70                  75                  80

Ala Ile Arg Arg Leu His Glu Ala Gly Val Ala Thr Met Thr Ala Val
                 85                  90                  95

Ala Tyr Gly Glu Arg Gly Ser Asp Pro Ala Arg Gln His Ser Phe Ile
            100                 105                 110

Val Thr Glu Glu Leu Ala Pro Thr Val Asp Leu Glu Val Phe Ser Gln
        115                 120                 125

Asp Trp Arg Glu Arg Pro Pro Pro Arg Leu Lys Arg Ala Leu Val
    130                 135                 140

Glu Ala Val Ala Arg Met Val Gly Asp Met His Arg Ala Gly Val Asn
145                 150                 155                 160

His Arg Asp Cys Tyr Ile Cys His Phe Leu Leu His Thr Asp Lys Pro
                165                 170                 175

Val Ser Ala Asp Asp Phe Arg Leu Ser Val Ile Asp Leu His Arg Ala
            180                 185                 190

Gln Thr Arg Asp Ala Thr Pro Lys Arg Trp Arg Asn Lys Asp Leu Ala
        195                 200                 205

Ala Leu Tyr Phe Ser Ala Leu Asp Ile Gly Leu Thr Arg Arg Asp Lys
    210                 215                 220

Leu Arg Phe Leu Arg Thr Tyr Phe Arg Arg Pro Leu Arg Glu Ile Leu
225                 230                 235                 240

Arg Asp Glu Ala Gly Leu Leu Ala Trp Met Glu Arg Gln Ala Glu Lys
                245                 250                 255

Leu Tyr Glu Arg Lys Gln Arg Tyr Gly Asp Leu Leu
            260                 265
```

<210> SEQ ID NO 3
<211> LENGTH: 1038
<212> TYPE: DNA
<213> ORGANISM: Pseudomonas aeruginosa rfaF (waaF)
<220> FEATURE:
<223> OTHER INFORMATION: Description of Organism: Pseudomonas aeruginosa serotype O5 strain PAO1

<400> SEQUENCE: 3

-continued

```
atgagaattc tgatcgtagg tccctcctgg gtgggggaca tggtgatggc gcagaccctg      60
ttccagtgtc tgcgccagcg gcatcccgag tgcgtgatcg acgtgctggc gcccgagtgg     120
agccgaccga tcctcgagcg catgcccgag gtgcgccagg ccctgagctt ccgctcggc      180 cacggggtga tggacgtcgc cacacggcgc cggatcggac gcggcctgcg cggtcagtac     240
gagcaggcga tcctgctgcc caactcgctg aagtcggcgc tggtgccctg gttcgccgga     300
ataccgaagc gtaccggctg gcgcggcgag atgcgctacg gctgctcaa tgacatccgc      360 aagctcgaca gcagcgcta tccgctgatg atcgaacgct tcatggccct ggccttcgag      420
ccgggcgtgg agttgccgaa gccctatccg cagccgcgcc tgcggatcga cgacggcagc     480
cgccaggcgg cgctcgacaa gttcgccctg agcctggacc gccgggtgct ggcgctctgt     540
cccggcgccg agttcggcga ggccaagcgc tggccggcgg aacactacgc cgcggtcgcc     600
gaggcgaaga tccgtgccgg ctggcaggtc tggctgttcg gctcgaagaa cgaccatccc     660
ggtggagagg agattcgcca gcgcctgatt ccggggttgc gcgaggagtc cttcaatctt     720
gccggggaga cttcgctggc cgaggccatc gacctgatgt cctgcgctgg cgcggtggtg     780
tccaacgatt ccggcctgat gcacgtggcg gccgcgctgg atcgcccgct ggtgggcgtc     840
tatggctcca cctcgccgca gttcacccccg ccgctggcgg accgggtgga gatcgtccgc     900
ctcggtctcg agtgcagccc gtgcttcgag cgcacctgtc gcttcggcca ctacaattgc     960
ctccgcgagc tgccgcctgg cctggtattg caagccctgg agcggctggt cggcgaccct    1020
gccgaggtcg ccggatga                                                   1038
```

<210> SEQ ID NO 4
<211> LENGTH: 345
<212> TYPE: PRT
<213> ORGANISM: Pseudomonas aeruginosa RfaF (WaaF)
<220> FEATURE:
<223> OTHER INFORMATION: Description of Organism: Pseudomonas aeruginosa
    serotype O5 strain PAO1

<400> SEQUENCE: 4

```
Met Arg Ile Leu Ile Val Gly Pro Ser Trp Val Gly Asp Met Val Met
 1               5                  10                  15

Ala Gln Thr Leu Phe Gln Cys Leu Arg Gln Arg His Pro Glu Cys Val
            20                  25                  30

Ile Asp Val Leu Ala Pro Glu Trp Ser Arg Pro Ile Leu Glu Arg Met
        35                  40                  45

Pro Glu Val Arg Gln Ala Leu Ser Phe Pro Leu Gly His Gly Val Met
    50                  55                  60

Asp Val Ala Thr Arg Arg Arg Ile Gly Arg Gly Leu Arg Gly Gln Tyr
65                  70                  75                  80

Glu Gln Ala Ile Leu Leu Pro Asn Ser Leu Lys Ser Ala Leu Val Pro
                85                  90                  95

Trp Phe Ala Gly Ile Pro Lys Arg Thr Gly Trp Arg Gly Glu Met Arg
            100                 105                 110

Tyr Gly Leu Leu Asn Asp Ile Arg Lys Leu Asp Lys Gln Arg Tyr Pro
        115                 120                 125

Leu Met Ile Glu Arg Phe Met Ala Leu Ala Phe Glu Pro Gly Val Glu
    130                 135                 140

Leu Pro Lys Pro Tyr Pro Gln Pro Arg Leu Arg Ile Asp Asp Gly Ser
145                 150                 155                 160

Arg Gln Ala Ala Leu Asp Lys Phe Ala Leu Ser Leu Asp Arg Pro Val
                165                 170                 175
```

```
Leu Ala Leu Cys Pro Gly Ala Glu Phe Gly Glu Ala Lys Arg Trp Pro
            180                 185                 190
Ala Glu His Tyr Ala Ala Val Ala Glu Ala Lys Ile Arg Ala Gly Trp
        195                 200                 205
Gln Val Trp Leu Phe Gly Ser Lys Asn Asp His Pro Gly Gly Glu Glu
    210                 215                 220
Ile Arg Gln Arg Leu Ile Pro Gly Leu Arg Glu Ser Phe Asn Leu
225                 230                 235                 240
Ala Gly Glu Thr Ser Leu Ala Glu Ala Ile Asp Leu Met Ser Cys Ala
                245                 250                 255
Gly Ala Val Val Ser Asn Asp Ser Gly Leu Met His Val Ala Ala Ala
            260                 265                 270
Leu Asp Arg Pro Leu Val Gly Val Tyr Gly Ser Thr Ser Pro Gln Phe
        275                 280                 285
Thr Pro Pro Leu Ala Asp Arg Val Glu Ile Val Arg Leu Gly Leu Glu
    290                 295                 300
Cys Ser Pro Cys Phe Glu Arg Thr Cys Arg Phe Gly His Tyr Asn Cys
305                 310                 315                 320
Leu Arg Glu Leu Pro Pro Gly Leu Val Leu Gln Ala Leu Glu Arg Leu
                325                 330                 335
Val Gly Asp Pro Ala Glu Val Ala Gly
            340                 345

<210> SEQ ID NO 5
<211> LENGTH: 1068
<212> TYPE: DNA
<213> ORGANISM: Pseudomonas aeruginosa rfaC (WaaC)
<220> FEATURE:
<223> OTHER INFORMATION: Description of Organism: Pseudomonas aeruginosa
      serotype O5 strain PAO1

<400> SEQUENCE: 5
atgagggtgc tgctggtcaa gacctcgtcc ctcggcgacg tgatccacac cctgccggcg      60
cttaccgacg ccgcccgggc gattcccggc atccagttcg actgggtggt ggaggaaggt    120
ttcgccgaga ttcccgcctg gcatccggcg gtggcgcggg tgatcccggt ggcgatccgg    180
cgctggcgca agaacctctg gcagaccctg cgcaacggcg aatggcggcg cttcaagcag    240
cgcctgaagg aagtcgacta tgacctggtg atcgacgccc aggggctgct gaagagtgcc    300
tggctgaccc gctacgtggg caagacgccg gtcgccggtc tcgatcgcga ctcggcgcgc    360
gagccgctcg ccagccgctt ctatcgccgt gcctatccgg tcgcctgggg acagcatgcg    420
gtggagcgca cgcgccagtt gttcgcccag gcgctggact cccgttgcc cgagtcggtc    480 ggtgaatatg gcctggaccg cgagcagttg gccgacgccg accctggcgc gccgtacctg    540
gtgttcctgc acgtactac ctgggtcacc aagcattggc cggaagccta ctggcgcgaa    600
ctggccgagc gcatgtgcga gcgcggctgg tcggtgcgcc tgccctgggg cagcgccgcc    660
gagcgggagc gggccgggcg cctggcggcg gggttggaaa atgccgcggt actccccaga    720
ttatccctgg ccggcatggc caaggtgctt gccggcgcgc gcgcctgcgt ggcggtggat    780 accgcctcg gtcacctggc ggcggcgctg gacgtgccga cgctgtcgct gttcggcccg    840
accaatcctg gcttcaccgg cgcctacggg cgttcccagg tccacctggg cagcgacttc    900
ccctgtgcgc cgtgcctgaa gaagacttgt acctaccagc cgaccgaaga ggatcgcaaa    960
ctgttcgatc tcaagcgtga gcagccgctg tgcttcaccc ggctgaatcc ccagcgcgtg   1020
```

```
gccacccagc tggaggccat gctgctggcc ccggagaccc tccgatga            1068
```

<210> SEQ ID NO 6
<211> LENGTH: 355
<212> TYPE: PRT
<213> ORGANISM: Pseudomonas aeruginosa RfaC (WaaC)
<220> FEATURE:
<223> OTHER INFORMATION: Description of Organism: Pseudomonas aeruginosa serotype O5 strain PAO1

<400> SEQUENCE: 6

```
Met Arg Val Leu Leu Val Lys Thr Ser Ser Leu Gly Asp Val Ile His
 1               5                  10                  15

Thr Leu Pro Ala Leu Thr Asp Ala Ala Arg Ala Ile Pro Gly Ile Gln
            20                  25                  30

Phe Asp Trp Val Val Glu Glu Gly Phe Ala Glu Ile Pro Ala Trp His
        35                  40                  45

Pro Ala Val Ala Arg Val Ile Pro Val Ala Ile Arg Arg Trp Arg Lys
    50                  55                  60

Asn Leu Trp Gln Thr Leu Arg Asn Gly Glu Trp Arg Arg Phe Lys Gln
65                  70                  75                  80

Arg Leu Lys Glu Val Asp Tyr Asp Leu Val Ile Asp Ala Gln Gly Leu
                85                  90                  95

Leu Lys Ser Ala Trp Leu Thr Arg Tyr Val Gly Lys Thr Pro Val Ala
            100                 105                 110

Gly Leu Asp Arg Asp Ser Ala Arg Glu Pro Leu Ala Ser Arg Phe Tyr
        115                 120                 125

Arg Arg Ala Tyr Pro Val Ala Trp Gly Gln His Ala Val Glu Arg Thr
    130                 135                 140

Arg Gln Leu Phe Ala Gln Ala Leu Asp Tyr Pro Leu Pro Glu Ser Val
145                 150                 155                 160

Gly Glu Tyr Gly Leu Asp Arg Glu Gln Leu Ala Asp Ala Asp Pro Gly
                165                 170                 175

Ala Pro Tyr Leu Val Phe Leu His Gly Thr Thr Trp Val Thr Lys His
            180                 185                 190

Trp Pro Glu Ala Tyr Trp Arg Glu Leu Ala Glu Arg Met Cys Glu Arg
        195                 200                 205

Gly Trp Ser Val Arg Leu Pro Trp Gly Ser Ala Ala Glu Arg Glu Arg
    210                 215                 220

Ala Gly Arg Leu Ala Ala Gly Leu Glu Asn Ala Ala Val Leu Pro Arg
225                 230                 235                 240

Leu Ser Leu Ala Gly Met Ala Lys Val Leu Ala Gly Ala Arg Ala Cys
                245                 250                 255

Val Ala Val Asp Thr Gly Leu Gly His Leu Ala Ala Leu Asp Val
            260                 265                 270

Pro Thr Leu Ser Leu Phe Gly Pro Thr Asn Pro Gly Phe Thr Gly Ala
        275                 280                 285

Tyr Gly Arg Ser Gln Val His Leu Gly Ser Asp Phe Pro Cys Ala Pro
    290                 295                 300

Cys Leu Lys Lys Thr Cys Thr Tyr Gln Pro Thr Glu Glu Asp Arg Lys
305                 310                 315                 320

Leu Phe Asp Leu Lys Arg Glu Gln Pro Leu Cys Phe Thr Arg Leu Asn
                325                 330                 335

Pro Gln Arg Val Ala Thr Gln Leu Glu Ala Met Leu Leu Ala Pro Glu
            340                 345                 350
```

Thr Leu Arg
    355

<210> SEQ ID NO 7
<211> LENGTH: 1122
<212> TYPE: DNA
<213> ORGANISM: Pseudomonas aeruginosa rfaG (waaG)
<220> FEATURE:
<223> OTHER INFORMATION: Description of Organism: Pseudomonas aeruginosa
      serotype O5 strain PAO1

<400> SEQUENCE: 7
atgaccctgg cgttcatcct ctacaaatac ttccccttcg gcggcctgca gcgtgacttc      60
atgcgcatcg ccctggaatg ccagcggcgc gggcacgaca tccgcgtcta ccctgatc      120
tgggagggcg acgtgccgga cggcttcgaa gtgctggtgg ccccggtgcg ctcgatcttc     180
aaccaccggc gcaacgagaa gttcaccgcg tgggtccgcg ccgacctgga caggcgcccg     240
gtgcagcggg tgatcggctt caacaagatg cccggactgg atgtctacta cgccgccgac     300
gcctgtttcg aggaaaaggc ccagaccttg cgcaacccgc tgtaccgcca gtggggccgc     360
taccgccact tcgccggcta cgaacgggca gtgttcgacc cggcctcgaa gaccgagatc     420
ctgatgatct ccgaggtgca gcagccgctc ttggtcaagc actacggcac ccaggccgag     480
cgtttccatc tgctgccgcc ggggatcagc caggatcgcg ggcgccggc caacgccgcg     540
gacgtgcgtg cggaattccg ccgcgagttc ggcctggagg aggacgacct gctgctggtg     600
cagatcggtt ccggcttcaa gaccaagggc ctggatcgca gcctgaaggc gctgtccgcg     660
ctgcccaagg cgttgcgcag gcgtacccgg ctgatcgcca tcggccagga cgatcccaag     720
ccgttcctgc tacagatcgc cgccctcggt ctcaacgacc aggtacagat cctcaagggg     780
cgcagcgata tcccgcgctt cctgctcggc gccgacctgc tgatccaccc ggcctacaac     840
gagaacaccg gtacggtgct gctggaggcg ctggtctccg gcctgccggt gttggtgacc     900
gatgtctgcg gctatgccca ctacatcgcc gaggccgacg ccgggcgggt gctgccgagt     960
cccttcgagc aggacagtct caaccgcctg ctcgcgaaa tgctggagga cgctccggcg    1020
cgcgccgcct ggtcgcgcaa tggcctggcc tacgccgatc acgccgacct ctacagcatg    1080
ccgcagcgcg ccgccgacct gatcctcggg gaggcctcat ga                       1122

<210> SEQ ID NO 8
<211> LENGTH: 373
<212> TYPE: PRT
<213> ORGANISM: Pseudomonas aeruginosa RFaG (WaaG)
<220> FEATURE:
<223> OTHER INFORMATION: Description of Organism: Pseudomonas aeruginosa
      serotype O5 strain PAO1

<400> SEQUENCE: 8

Met Thr Leu Ala Phe Ile Leu Tyr Lys Tyr Phe Pro Phe Gly Gly Leu
 1               5                  10                  15

Gln Arg Asp Phe Met Arg Ile Ala Leu Glu Cys Gln Arg Arg Gly His
            20                  25                  30

Asp Ile Arg Val Tyr Thr Leu Ile Trp Glu Gly Asp Val Pro Asp Gly
        35                  40                  45

Phe Glu Val Leu Val Ala Pro Val Arg Ser Ile Phe Asn His Arg Arg
    50                  55                  60

Asn Glu Lys Phe Thr Ala Trp Val Arg Ala Asp Leu Asp Arg Arg Pro
65                  70                  75                  80

Val Gln Arg Val Ile Gly Phe Asn Lys Met Pro Gly Leu Asp Val Tyr

-continued

|   |   |   |   |   | 85 |   |   |   |   | 90 |   |   |   |   | 95 |   |   |
|---|---|---|---|---|---|---|---|---|---|---|---|---|---|---|---|---|---|
| Tyr | Ala | Ala | Asp | Ala | Cys | Phe | Glu | Glu | Lys | Ala | Gln | Thr | Leu | Arg | Asn |
|   |   |   | 100 |   |   |   | 105 |   |   |   | 110 |   |   |   |   |
| Pro | Leu | Tyr | Arg | Gln | Trp | Gly | Arg | Tyr | Arg | His | Phe | Ala | Gly | Tyr | Glu |
|   |   | 115 |   |   |   | 120 |   |   |   | 125 |   |   |   |   |   |
| Arg | Ala | Val | Phe | Asp | Pro | Ala | Ser | Lys | Thr | Glu | Ile | Leu | Met | Ile | Ser |
|   | 130 |   |   |   |   | 135 |   |   |   | 140 |   |   |   |   |   |
| Glu | Val | Gln | Gln | Pro | Leu | Leu | Val | Lys | His | Tyr | Gly | Thr | Gln | Ala | Glu |
| 145 |   |   |   |   | 150 |   |   |   | 155 |   |   |   |   |   | 160 |
| Arg | Phe | His | Leu | Leu | Pro | Pro | Gly | Ile | Ser | Gln | Asp | Arg | Arg | Ala | Pro |
|   |   |   | 165 |   |   |   |   | 170 |   |   |   |   | 175 |   |   |
| Ala | Asn | Ala | Ala | Asp | Val | Arg | Ala | Glu | Phe | Arg | Arg | Glu | Phe | Gly | Leu |
|   |   | 180 |   |   |   |   | 185 |   |   |   |   | 190 |   |   |   |
| Glu | Glu | Asp | Asp | Leu | Leu | Leu | Val | Gln | Ile | Gly | Ser | Gly | Phe | Lys | Thr |
|   |   | 195 |   |   |   |   | 200 |   |   |   |   | 205 |   |   |   |
| Lys | Gly | Leu | Asp | Arg | Ser | Leu | Lys | Ala | Leu | Ser | Ala | Leu | Pro | Lys | Ala |
|   | 210 |   |   |   |   | 215 |   |   |   |   | 220 |   |   |   |   |
| Leu | Arg | Arg | Arg | Thr | Arg | Leu | Ile | Ala | Ile | Gly | Gln | Asp | Asp | Pro | Lys |
| 225 |   |   |   |   | 230 |   |   |   |   | 235 |   |   |   |   | 240 |
| Pro | Phe | Leu | Leu | Gln | Ile | Ala | Ala | Leu | Gly | Leu | Asn | Asp | Gln | Val | Gln |
|   |   |   |   | 245 |   |   |   |   | 250 |   |   |   |   | 255 |   |
| Ile | Leu | Lys | Gly | Arg | Ser | Asp | Ile | Pro | Arg | Phe | Leu | Leu | Gly | Ala | Asp |
|   |   |   |   | 260 |   |   |   |   | 265 |   |   |   |   | 270 |   |
| Leu | Leu | Ile | His | Pro | Ala | Tyr | Asn | Glu | Asn | Thr | Gly | Thr | Val | Leu | Leu |
|   |   |   | 275 |   |   |   |   | 280 |   |   |   |   | 285 |   |   |
| Glu | Ala | Leu | Val | Ser | Gly | Leu | Pro | Val | Leu | Val | Thr | Asp | Val | Cys | Gly |
|   | 290 |   |   |   |   |   | 295 |   |   |   |   | 300 |   |   |   |
| Tyr | Ala | His | Tyr | Ile | Ala | Glu | Ala | Asp | Ala | Gly | Arg | Val | Leu | Pro | Ser |
| 305 |   |   |   |   | 310 |   |   |   |   | 315 |   |   |   |   | 320 |
| Pro | Phe | Glu | Gln | Asp | Ser | Leu | Asn | Arg | Leu | Leu | Ala | Glu | Met | Leu | Glu |
|   |   |   |   | 325 |   |   |   |   | 330 |   |   |   |   | 335 |   |
| Asp | Ala | Pro | Ala | Arg | Ala | Ala | Trp | Ser | Arg | Asn | Gly | Leu | Ala | Tyr | Ala |
|   |   |   |   | 340 |   |   |   |   | 345 |   |   |   |   | 350 |   |
| Asp | His | Ala | Asp | Leu | Tyr | Ser | Met | Pro | Gln | Arg | Ala | Ala | Asp | Leu | Ile |
|   |   |   | 355 |   |   |   |   | 360 |   |   |   |   | 365 |   |   |
| Leu | Gly | Glu | Ala | Ser |
|   | 370 |   |   |   |